United States Patent
Hirokawa et al.

(10) Patent No.: US 11,419,495 B2
(45) Date of Patent: Aug. 23, 2022

(54) IMAGE PROCESSING METHOD, IMAGE PROCESSING DEVICE, AND STORAGE MEDIUM

(71) Applicant: NIKON CORPORATION, Tokyo (JP)

(72) Inventors: Mariko Hirokawa, Yokohama (JP); Yasushi Tanabe, Fujisawa (JP); Tomoharu Fujiwara, Gyoda (JP)

(73) Assignee: NIKON CORPORATION, Tokyo (JP)

( * ) Notice: Subject to any disclaimer, the term of this patent is extended or adjusted under 35 U.S.C. 154(b) by 178 days.

(21) Appl. No.: 16/669,109

(22) Filed: Oct. 30, 2019

(65) Prior Publication Data
US 2021/0127970 A1    May 6, 2021

(51) Int. Cl.
  A61B 3/12   (2006.01)
  A61B 3/10   (2006.01)
  A61B 3/00   (2006.01)

(52) U.S. Cl.
  CPC .......... *A61B 3/1233* (2013.01); *A61B 3/0058* (2013.01); *A61B 3/102* (2013.01)

(58) Field of Classification Search
  CPC ...... A61B 3/1233; A61B 3/102; A61B 3/0058
  USPC ....................................................... 351/206
  See application file for complete search history.

(56) References Cited

U.S. PATENT DOCUMENTS

| 10,916,012 | B2* | 2/2021 | Iwase ...................... G06T 7/136 |
| 2014/0185009 | A1* | 7/2014 | Imamura .............. A61B 3/1025 351/208 |
| 2014/0205169 | A1 | 7/2014 | Yamakawa et al. |
| 2015/0366452 | A1* | 12/2015 | Iwase .................. A61B 3/0025 351/206 |
| 2019/0274542 | A1* | 9/2019 | Imamura ................ A61B 3/102 |

FOREIGN PATENT DOCUMENTS

| JP | 2013-154120 A | 8/2013 |
| JP | 2014-140490 A | 8/2014 |

OTHER PUBLICATIONS

Office Action for Japanese Patent Application No. 2018-192509 dated May 24, 2022.

* cited by examiner

*Primary Examiner* — Mohammed A Hasan
(74) *Attorney, Agent, or Firm* — Foley & Lardner LLP

(57) ABSTRACT

An image processing method, which is executed by a processor, comprises acquiring choroid information from an image of a fundus of an examined eye, and comparing the choroid information against a choroid normative database and determining whether or not there is an abnormality in the fundus.

11 Claims, 20 Drawing Sheets

CHOROIDAL VASCULAR
IMAGE

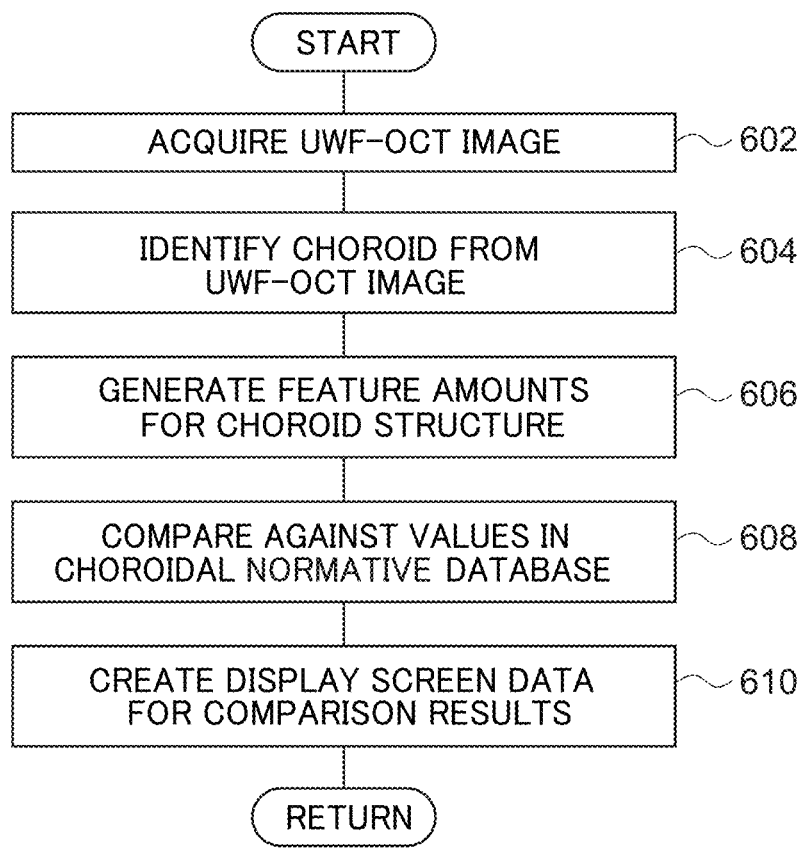

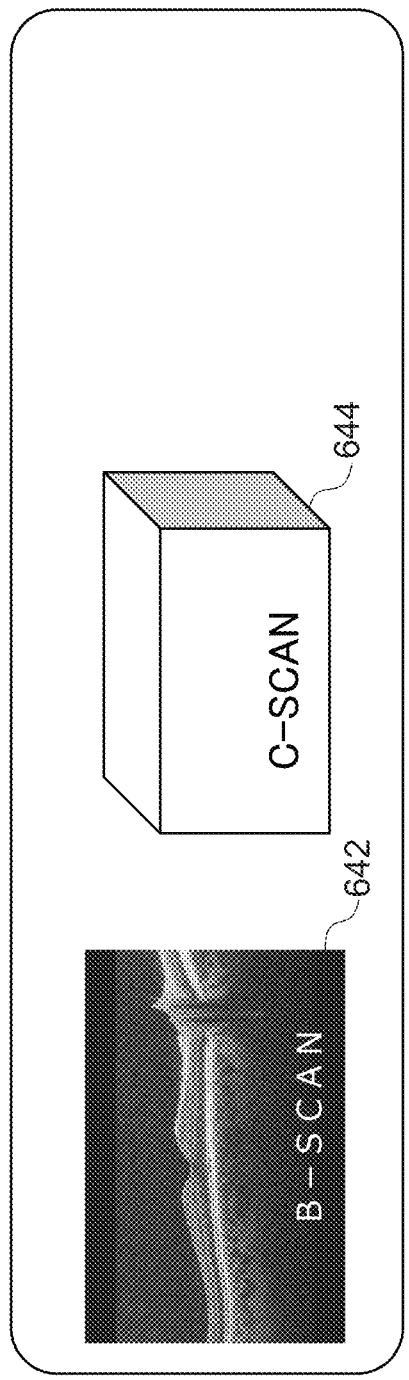

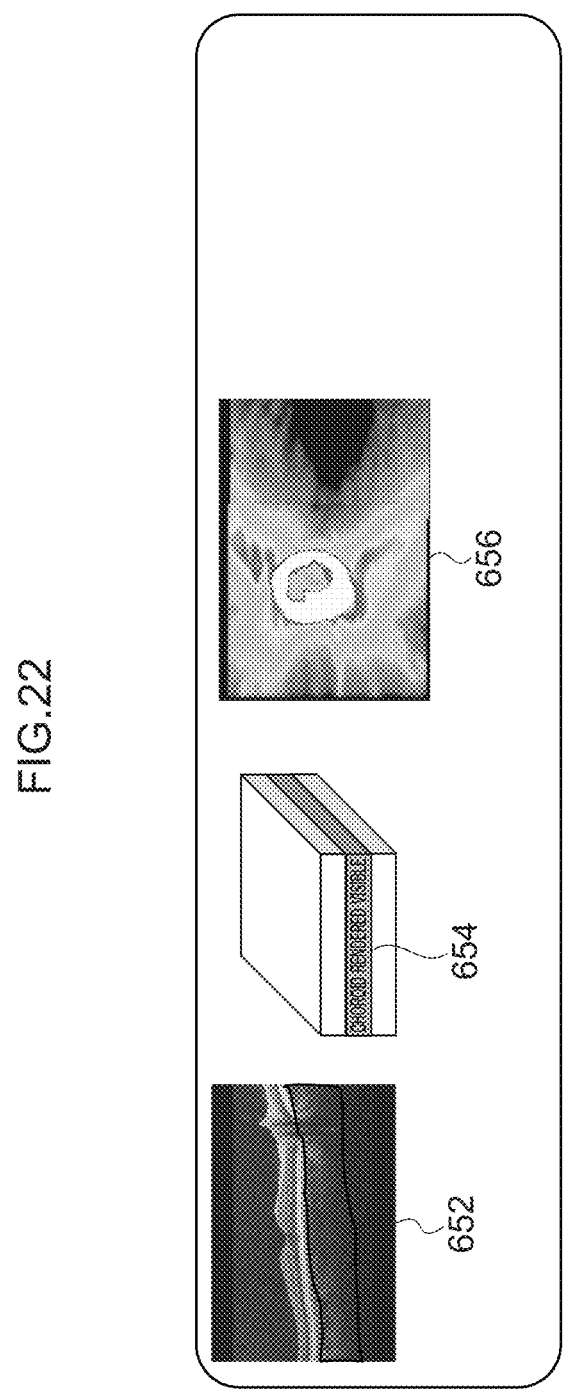

FIG.23

| JAPANESE MALE IN 20S | | STANDARD VALUE | DETERMINATION CONDITIONS |
|---|---|---|---|
| FEATURE AMOUNTS OBTAINED FROM SLO IMAGE | VORTEX VEIN POSITIONS | | |
| | DEGREE OF SYMMETRY OF VORTEX VEIN POSITIONS | | |
| | BLOOD VESSEL DIAMETERS IN VORTEX VEIN VICINITY POSITIONS    HISTOGRAM    AVERAGE VALUE | | |
| | BLOOD VESSEL DIAMETERS OF ALL CHOROID    HISTOGRAM    AVERAGE VALUE | | |
| | DEGREE OF MEANDERING OF EACH CHOROIDAL BLOOD VESSEL | | |
| | DEGREE OF ASYMMETRY IN CHOROIDAL BLOOD VESSELS | | |
| | ⋮ | | |
| FEATURE AMOUNTS OBTAINED FROM OCT IMAGE | CHOROID THICKNESS | | |
| | DEGREE OF PROJECTION | | |
| | DEGREE OF WAVINESS | | |
| | LUMEN/STROMA RATIO | | |
| | PERFUSION DENSITY | | |
| | | | |
| ICGA IMAGE | PULSE OF PULSATILE POLYPS | | |
| | CHOROIDAL CAPILLARY FILLING DELAY | | |
| | ⋮ | | |
| JAPANESE MALE IN 30S | | | |

⋮

IMAGE PROCESSING METHOD, IMAGE PROCESSING DEVICE, AND STORAGE MEDIUM

CROSS-REFERENCE TO RELATED APPLICATION

This application is based on Japanese Patent Application No. 2018-192509 filed on Oct. 11, 2018, the disclosure of which is incorporated by reference herein entirely.

BACKGROUND

Technical Field

Technology disclosed in the present disclosure relates to an image processing method, an image processing device, and a storage medium.

Related Art

The specification of US Patent Application Laid-Open No. 2015/0366452A1 discloses tomographic image analysis of a fundus and extraction of an anomalous region therein. There is a desire to be able to check an abnormality more easily.

SUMMARY

A first aspect of the present disclosure is an image processing method, which is executed by a processor, comprises acquiring choroid information from an image of a fundus of an examined eye, and comparing the choroid information against a choroid normative database and determining whether or not there is an abnormality in the fundus.

A second aspect of the present disclosure is an image processing device comprising memory and a processor coupled to the memory, wherein the processor is configured to acquire choroid information from an image of a fundus of an examined eye, and compare the choroid information against a choroid normative database and determine whether or not there is an abnormality in the fundus.

A third aspect of the present disclosure is a storage medium being not a transitory signal and stored with an image processing program that causes a computer to execute processing, the processing comprising acquiring choroid information from an image of a fundus of an examined eye, and comparing the choroid information against a choroid normative database and determining whether or not there is an abnormality in the fundus.

BRIEF DESCRIPTION OF THE DRAWINGS

Exemplary embodiments of the present invention will be described in detail based on the following figures, wherein:

FIG. 20 is a flowchart of UWF-OCT image processing performed at step 214 in FIG. 6;

FIG. 21 is a diagram illustrating an OCT image (B-SCAN image) 642 of a fundus acquired with reference to a straight line and three-dimensional OCT data 644 for a two-dimensional region acquired with reference to the two-dimensional region;

FIG. 22 is a diagram illustrating a choroid 652 obtained from the OCT image (B-SCAN image) 642, a choroid 654 obtained from the three-dimensional OCT data 644, and a thickness map 656 of choroid thickness;

FIG. 23 is a diagram illustrating contents stored in a normative database; and

DETAILED DESCRIPTION

Detailed explanation follows regarding exemplary embodiments of technology disclosed herein, with reference to the drawings.

Figure 1:
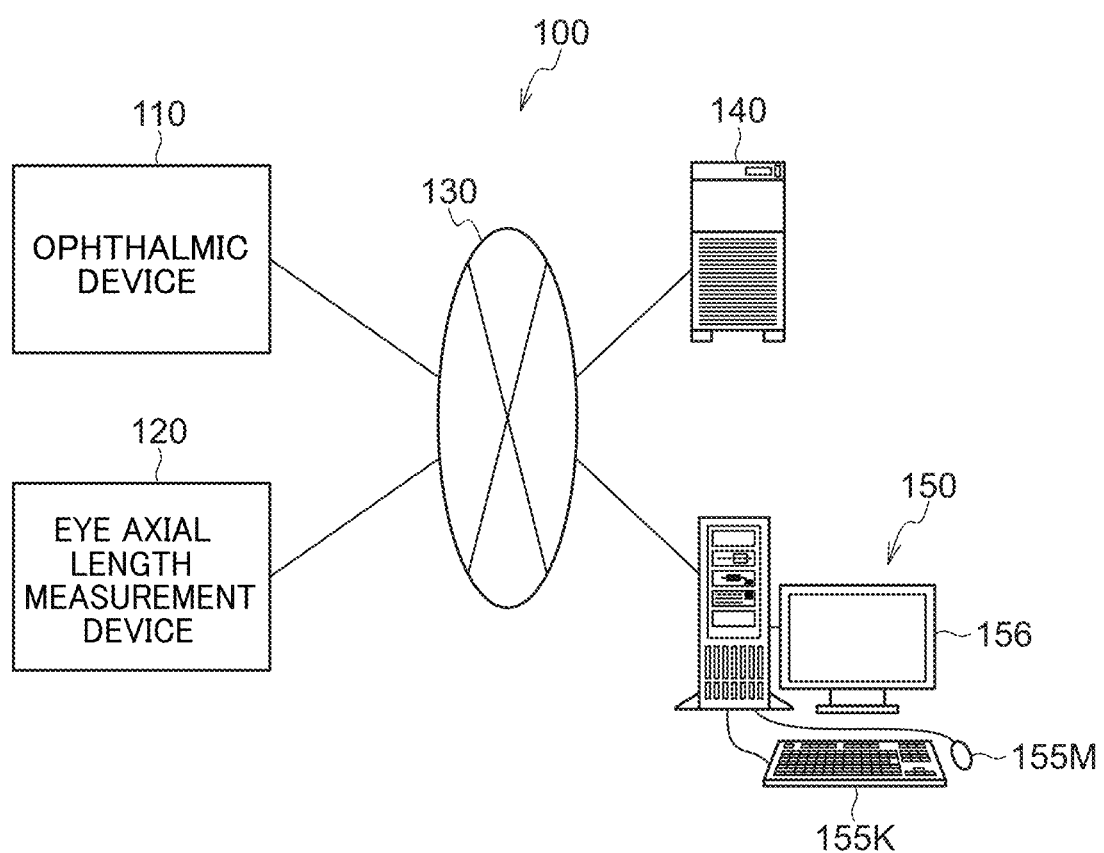
FIG. 1 is a block diagram of an ophthalmic system 100.

Configuration of an ophthalmic system 100 will now be explained with reference to FIG. 1. As illustrated in FIG. 1, the ophthalmic system 100 includes an ophthalmic device 110, an eye axial length measurement device 120, a management server device (referred to hereafter as "management server") 140, and an image display device (referred to hereafter as "image viewer") 150. The ophthalmic device 110 acquires an image of the fundus. The eye axial length measurement device 120 measures the axial length of the eye of a patient. The management server 140 stores plural fundus images, eye axial lengths, and tomographic images obtained by imaging the fundus of plural patients using the ophthalmic device 110, and stores these in association with patient IDs. The image viewer 150 displays fundus images acquired from the management server 140.

The ophthalmic device 110, the eye axial length measurement device 120, the management server 140, and the image viewer 150 are coupled together over a network 130.

The eye axial length measurement device 120 has two modes for measuring eye axial length, this being the length of an examined eye 12 in an eye axial direction: a first mode and a second mode. In the first mode, after light from a non-illustrated light source is guided into the examined eye 12, interference between light reflected from the fundus and light reflected from the cornea is photo-detected as interference light, and the eye axial length is measured based on an interference signal representing the photo-detected interference light. The second mode is a mode to measure the eye axial length by employing non-illustrated ultrasound waves.

The eye axial length measurement device 120 transmits the eye axial length as measured using either the first mode or the second mode to the management server 140. The eye axial length may be measured using both the first mode and the second mode, and in such cases, an average of the eye axial lengths as measured using the two modes is transmitted to the management server 140 as the eye axial length.

Figure 2:
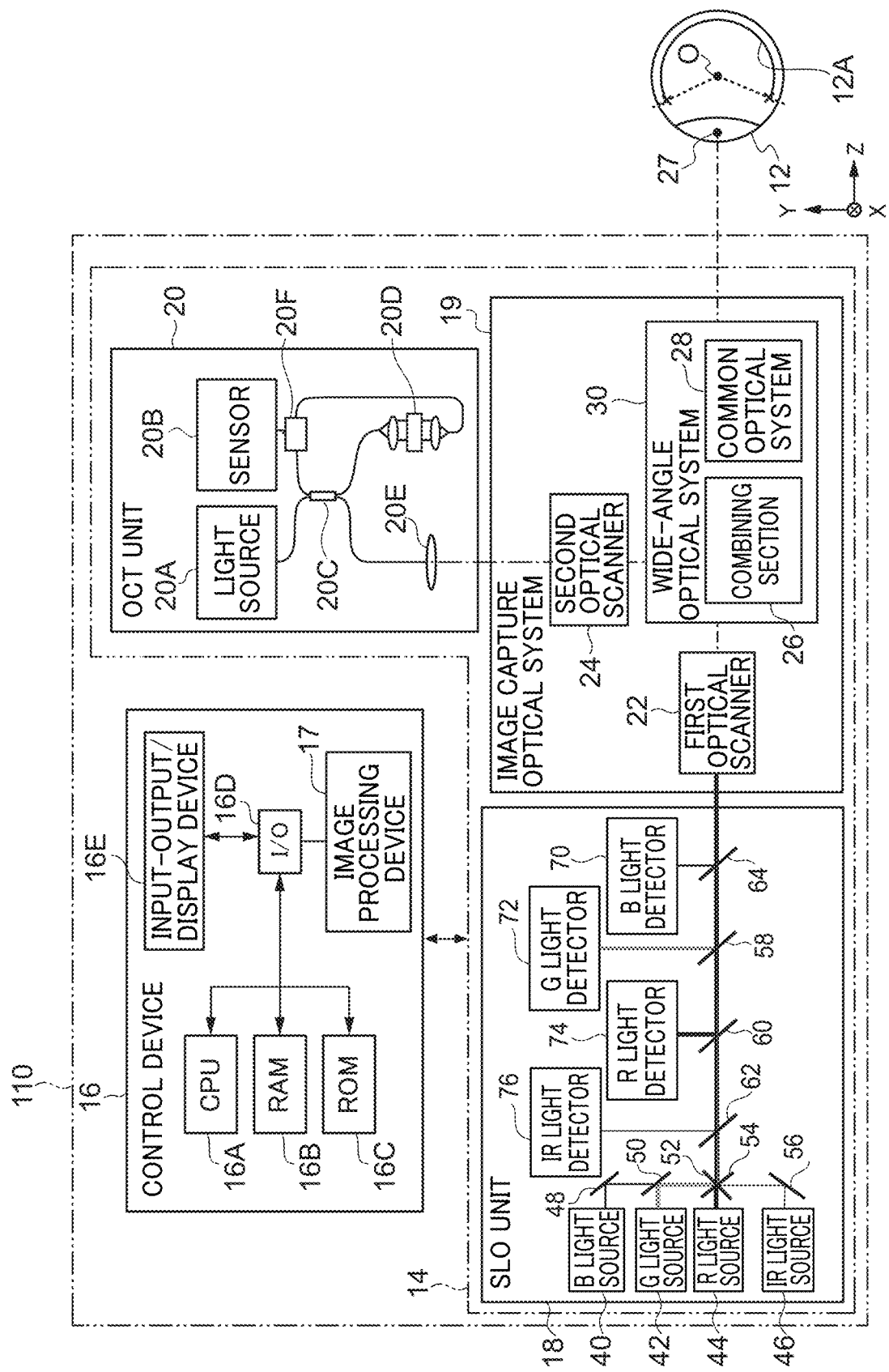
FIG. 2 is a schematic configuration diagram illustrating an overall configuration of an ophthalmic device 110.

Explanation follows regarding configuration of the ophthalmic device 110, with reference to FIG. 2.

For ease of explanation, scanning laser ophthalmoscope is abbreviated to SLO, and optical coherence tomography is abbreviated to OCT.

In cases in which the ophthalmic device 110 is installed on a horizontal plane with a horizontal direction taken as an X direction, a direction perpendicular to the horizontal plane is denoted as being a Y direction, and a direction connecting the center of the pupil at the anterior segment of the examined eye 12 and the center of the eyeball is denoted as being a Z direction. The X direction, the Y direction, and the Z direction are thus mutually perpendicular directions.

The ophthalmic device 110 includes an imaging device 14 and a control device 16. The imaging device 14 is provided with an SLO unit 18 and an OCT unit 20, and acquires a fundus image of the fundus of the examined eye 12. Two-dimensional fundus images that have been acquired by the SLO unit 18 are referred to hereafter as SLO images. Tomographic images, face-on images (en-face images) and the like of the retina created based on OCT data acquired by the OCT unit 20 are referred to hereafter as OCT images.

The control device 16 includes a computer provided with a Central Processing Unit (CPU) 16A, Random Access Memory (RAM) 16B, Read-Only Memory (ROM) 16C, and an input/output (I/O) port 16D.

The control device 16 is provided with an input-output/display device 16E coupled to the CPU 16A through the I/O port 16D. The input-output/display device 16E includes a graphical user interface to display images of the examined eye 12 and to receive various instructions from a user. An example of the graphical user interface is a touch panel display.

The control device 16 is provided with an image processing device 17 coupled to the I/O port 16D. The image processing device 17 generates images of the examined eye 12 based on data acquired by the imaging device 14. Note that the control device 16 is coupled to the network 130 through a communication interface, not illustrated in the drawings.

Although the control device 16 of the ophthalmic device 110 is provided with the input-output/display device 16E as illustrated above in FIG. 2, the technology disclosed herein is not limited thereto. For example, a configuration may be adopted in which the control device 16 of the ophthalmic device 110 is not provided with the input-output/display device 16E, and instead a separate input-output/display device is provided that is physically independent of the ophthalmic device 110. In such cases, the display device is provided with an image processing processor unit that operates under the control of a display control section 204 of the CPU 16A in the control device 16. Such an image processing processor unit may display SLO images and the like based on an image signal output as an instruction by the display control section 204.

The imaging device 14 operates under the control of an imaging control section 202 of the control device 16. The imaging device 14 includes the SLO unit 18, an image capture optical system 19, and the OCT unit 20. The image capture optical system 19 includes a first optical scanner 22, a second optical scanner 24, and a wide-angle optical system 30.

The first optical scanner 22 scans light emitted from the SLO unit 18 two dimensionally in the X direction and the Y direction. The second optical scanner 24 scans light emitted from the OCT unit 20 two dimensionally in the X direction and the Y direction. As long as the first optical scanner 22 and the second optical scanner 24 are optical elements capable of polarizing light beams, they may be configured by any out of, for example, polygon mirrors, mirror galvanometers, or the like. A combination thereof may also be employed.

The wide-angle optical system 30 includes an objective optical system (not illustrated in FIG. 2) provided with a common optical system 28, and a combining section 26 that combines light from the SLO unit 18 with light from the OCT unit 20.

The objective optical system of the common optical system 28 may be a reflection optical system employing a concave mirror such as an elliptical mirror, a refractive optical system employing a wide-angle lens, or may be a reflection-refractive optical system employing a combination of a concave mirror and a lens. Employing a wide-angle optical system that utilizes an elliptical mirror, wide-angle lens, or the like enables imaging to be performed of not only a central portion of the fundus, but also of the retina at the periphery of the fundus.

For a system including an elliptical minor, a configuration may be adopted that utilizes an elliptical mirror system as disclosed in International Publication (WO) Nos. 2016/103484 or 2016/103489. The disclosures of WO Nos. 2016/103484 or 2016/103489 are incorporated in their entirety by reference herein.

Observation of the fundus over a wide field of view (FOV) 12A is implemented by employing the wide-angle optical system 30. The FOV 12A refers to a range capable of being imaged by the imaging device 14. The FOV 12A may be expressed as a viewing angle. In the present exemplary embodiment the viewing angle may be defined in terms of an internal illumination angle and an external illumination angle. The external illumination angle is the angle of illumination by a light beam shone from the ophthalmic device 110 toward the examined eye 12, and is an angle of illumination defined with respect to a pupil 27. The internal illumination angle is the angle of illumination of a light beam shone onto the fundus F, and is an angle of illumination defined with respect to an eyeball center O. A correspondence relationship exists between the external illumination angle and the internal illumination angle. For example, an external illumination angle of 120° is equivalent to an internal illumination angle of approximately 160°. The internal illumination angle in the present exemplary embodiment is 200°.

SLO fundus images obtained by imaging at an imaging angle having an internal illumination angle of 160° or greater are referred to as UWF-SLO fundus images. UWF is an abbreviation of ultra wide field.

An SLO system is realized by the control device 16, the SLO unit 18, and the image capture optical system 19 as illustrated in FIG. 2. The SLO system is provided with the wide-angle optical system 30, enabling fundus imaging over the wide FOV 12A.

The SLO unit 18 is provided with a blue (B) light source 40, a green (G) light source 42, a red (R) light source 44, an infrared (for example near infrared) (IR) light source 46, and optical systems 48, 50, 52, 54, 56 to guide the light from the light sources 40, 42, 44, 46 onto a single optical path using transmission or reflection. The optical systems 48, 50, 56 are configured by mirrors, and the optical systems 52, 54 are configured by beam splitters. B light is reflected by the optical system 48, is transmitted through the optical system 50, and is reflected by the optical system 54. G light is reflected by the optical systems 50, 54, R light is transmitted through the optical systems 52, 54, and IR light is reflected by the optical systems 52, 56. The respective lights are thereby guided onto a single optical path.

The SLO unit 18 is configured so as to be capable of switching between the light source or the combination of light sources employed for emitting laser light of different wavelengths, such as a mode in which R light and G light are emitted, a mode in which infrared light is emitted, etc. Although the example in FIG. 2 includes three light sources, i.e. the G light source 42, the R light source 44, and the IR light source 46, the technology disclosed herein is not limited thereto. For example, the SLO unit 18 may, furthermore, also include a blue (B) light source or a white light source, in a configuration in which light is emitted in various modes, such as a mode in which G light, R light, and B light are emitted or a mode in which white light is emitted alone.

Light introduced to the image capture optical system 19 from the SLO unit 18 is scanned in the X direction and the Y direction by the first optical scanner 22. The scanning light passes through the wide-angle optical system 30 and the pupil 27 and is shone onto the fundus. Reflected light that has been reflected by the fundus passes through the wide-angle optical system 30 and the first optical scanner 22 and is introduced into the SLO unit 18.

The SLO unit 18 is provided with a beam splitter 64 and a beam splitter 58. From out of the light coming from the posterior segment (fundus) of the examined eye 12, the B light therein is reflected by the beam splitter 64 and light other than B light therein is transmitted by the beam splitter 64. From out of the light transmitted by the beam splitter 64, the G light therein is reflected by the beam splitter 58 and light other than G light therein is transmitted by the beam splitter 58. The SLO unit 18 is further provided with a beam splitter 60 that, from out of the light transmitted through the beam splitter 58, reflects R light therein and transmits light other than R light therein. The SLO unit 18 is provided with a beam splitter 62 that reflects IR light from out of the light transmitted through the beam splitter 60. The SLO unit 18 is provided with a B light detector 70 to detect B light reflected by the beam splitter 64, a G light detector 72 to detect G light reflected by the beam splitter 58, an R light detector 74 to detect R light reflected by the beam splitter 60, and an IR light detector 76 to detect IR light reflected by the beam splitter 62.

Light that has passed through the wide-angle optical system 30 and the first optical scanner 22 and been introduced into the SLO unit 18 (i.e. reflected light that has been reflected by the fundus) is reflected by the beam splitter 64 and photo-detected by the B light detector 70 when B light, and is reflected by the beam splitter 58 and photo-detected by the G light detector 72 when G light. When R light, the incident light is transmitted through the beam splitter 58, reflected by the beam splitter 60, and photo-detected by the R light detector 74. When IR light, the incident light is transmitted through the beam splitters 58, 60, reflected by the beam splitter 62, and photo-detected by the IR light detector 76. The image processing device 17 that operates under the control of the CPU 16A employs signals detected by the B light detector 70, the G light detector 72, the R light detector 74, and the IR light detector 76 to generate UWF-SLO images.

Figure 12:
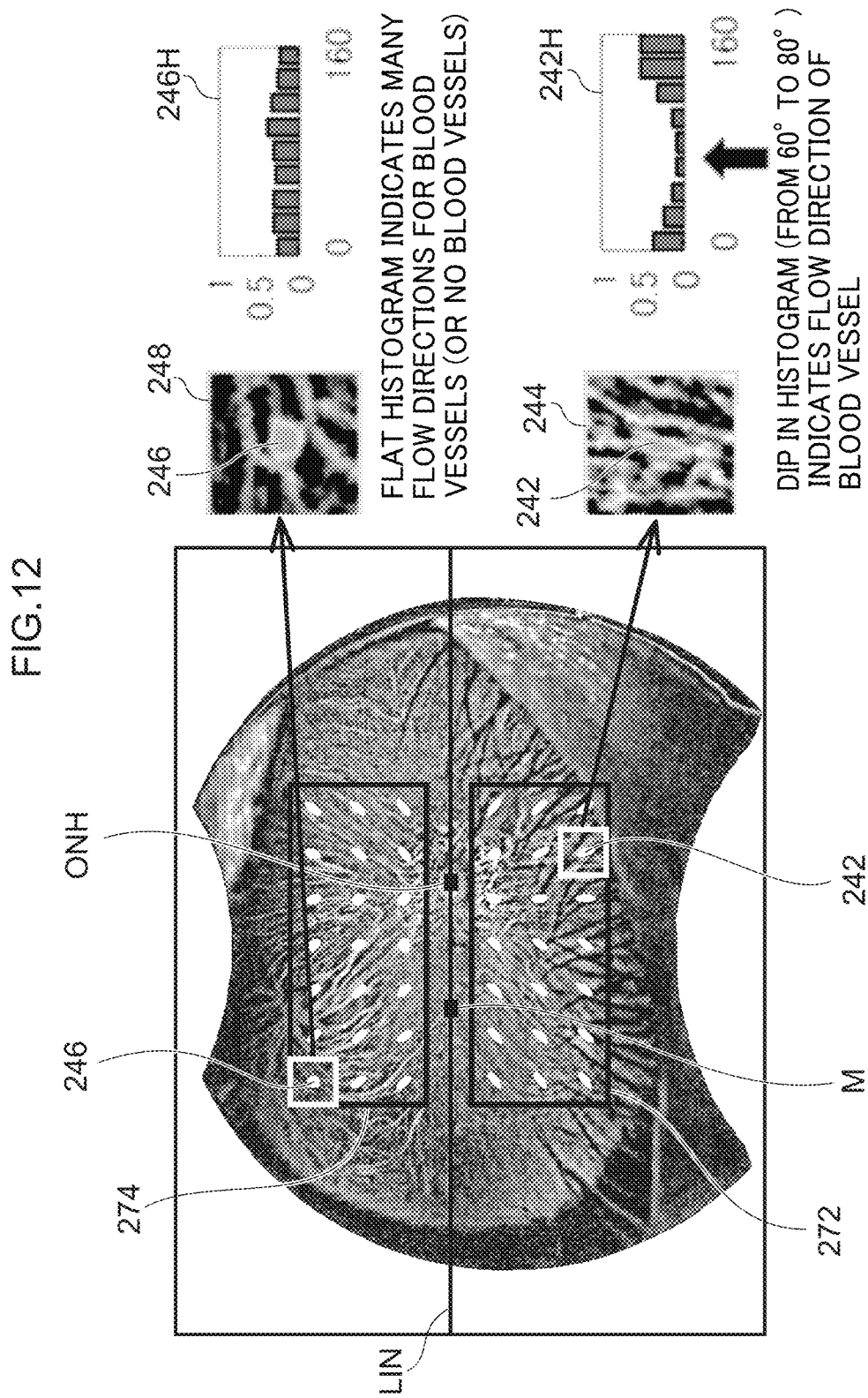
FIG. 12 is a diagram illustrating a region (cell) 244 configured by plural surrounding pixels centered on a central pixel corresponding to an analysis point 242.

As illustrated in FIG. 12, the UWF-SLO images include a UWF-SLO image (green fundus image) 502GG obtained by imaging the fundus in green, and a UWF-SLO image (red fundus image) 504RG obtained by imaging the fundus in red. The UWF-SLO images further include a UWF-SLO image (blue fundus image) 506BG obtained by imaging the fundus in blue, and a UWF-SLO image (IR fundus image) 508IRG obtained by imaging the fundus in IR.

The control device 16 may control the light sources 40, 42, 44 so as to emit light at the same time as each other. The green fundus image 502GG, the red fundus image 504RG, and the blue fundus image 506BG may be obtained at mutually corresponding each position by imaging the fundus of the examined eye 12 using B light, G light, and R light at the same time. An RGB color fundus image may be obtained from the green fundus image 502GG, the red fundus image 504RG, and the blue fundus image 506BG. The control device 16 may also control the light sources 42, 44 so as to emit light at the same time as each other. The green fundus image 502GG and the red fundus image 504RG are obtained at mutually corresponding positions by imaging the fundus of the examined eye 12 using G light and R light at the same time in this manner. An RG color fundus image may be obtained from the green fundus image 502GG and the red fundus image 504RG.

The UWF-SLO images further include an UWF-SLO image (video) 510ICGG imaged using ICG fluorescent light. When indocyanine green (ICG) is injected into a blood vessel so as to reach the fundus, the indocyanine green (ICG) first reaches the retina, then reaches the choroid, before passing through the choroid. The UWF-SLO image (video) 510ICGG is a video image from the time the indocyanine green (ICG) injected into a blood vessel reached the retina until after the indocyanine green (ICG) has passed through the choroid.

Each image data for the blue fundus image 506BG, the green fundus image 502GG, the red fundus image 504RG, the IR fundus image 508IRG, the RGB color fundus image, the RG color fundus image, and the UWF-SLO image 510ICGG are sent from the ophthalmic device 110 to the management server 140 through a non-illustrated communication IF.

An OCT system is realized by the control device 16, the OCT unit 20, and the image capture optical system 19 illustrated in FIG. 2. The OCT system is provided with the wide-angle optical system 30. This enables fundus imaging to be performed over the wide FOV 12A similarly to when imaging the SLO fundus images as described above. The OCT unit 20 includes a light source 20A, a sensor (detector) 20B, a first light coupler 20C, a reference optical system 20D, a collimator lens 20E, and a second light coupler 20F.

Light emitted from the light source 20A is split by the first light coupler 20C. After one part of the split light has been collimated by the collimator lens 20E into parallel light, to serve as measurement light, the parallel light is introduced into the image capture optical system 19. The measurement light is scanned in the X direction and the Y direction by the second optical scanner 24. The scanned light is shone onto the fundus through the wide-angle optical system 30 and the pupil 27. Measurement light that has been reflected by the fundus passes through the wide-angle optical system 30 and the second optical scanner 24 so as to be introduced into the OCT unit 20. The measurement light then passes through the collimator lens 20E and the first light coupler 20C before being incident to the second light coupler 20F.

The other part of the light emitted from the light source 20A and split by the first light coupler 20C is introduced into the reference optical system 20D as reference light, and is made incident to the second light coupler 20F through the reference optical system 20D.

The respective lights that are incident to the second light coupler 20F, namely the measurement light reflected by the fundus and the reference light, interfere with each other in the second light coupler 20F so as to generate interference light. The interference light is photo-detected by the sensor 20B. The image processing device 17 operating under the control of an image processing control section 206 generates OCT images, such as tomographic images and en-face images, based on OCT data detected by the sensor 20B.

OCT fundus images obtained by imaging at an imaging angle having an internal illumination angle of 160° or greater are referred to as UWF-OCT images.

Image data of the UWF-OCT images is sent from the ophthalmic device 110 to the management server 140 through the non-illustrated communication IF and stored in a storage device 254.

Note that although in the present exemplary embodiment an example is given in which the light source 20A is a swept-source OCT (SS-OCT), the light source 20A may be from various OCT systems, such as from of a spectral-domain OCT (SD-OCT) or a time-domain OCT (TD-OCT) system.

The eye axial length measurement device 120 in FIG. 1 includes the two modes for measuring the eye axial length, this being the length of the examined eye 12 in the eye axial direction (Z direction): the first mode and the second mode. In the first mode, after light from a non-illustrated light source has been guided into the examined eye 12, light arising from interference between the reflected light from the fundus and the reflected light from the cornea is photo-detected, and the eye axial length is measured based on an interference signal as expressed by the photo-detected interference light. The second mode is a mode in which the eye axial length is measured using ultrasound waves, not illustrated in the drawings. The eye axial length measurement device 120 transmits the eye axial length as measured using the first mode or the second mode to the management server 140. The eye axial length may be measured using both the first mode and the second mode, and in such cases an average of the eye axial length as measured using the two modes is transmitted as the eye axial length to the management server 140. The eye axial length is one type of data about a subject, and the eye axial length is saved as patient information in the management server 140 as well as being utilized in fundus image analysis.

Figure 3:
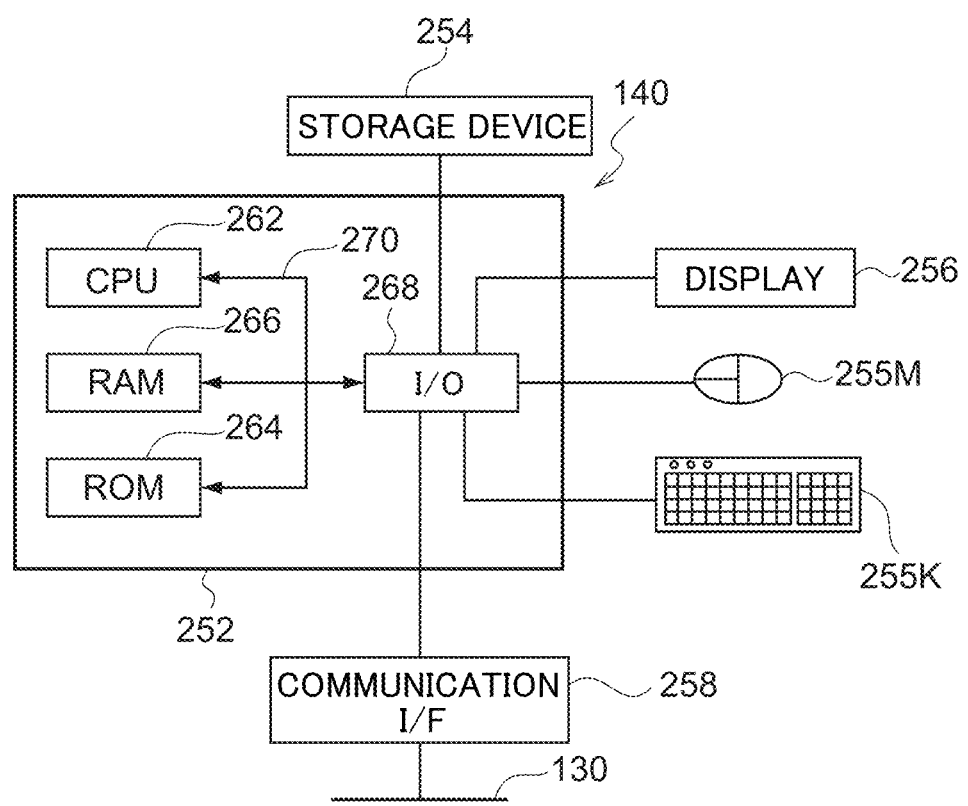
FIG. 3 is a block diagram of configuration of an electrical system of a management server 140.
Figure 4:
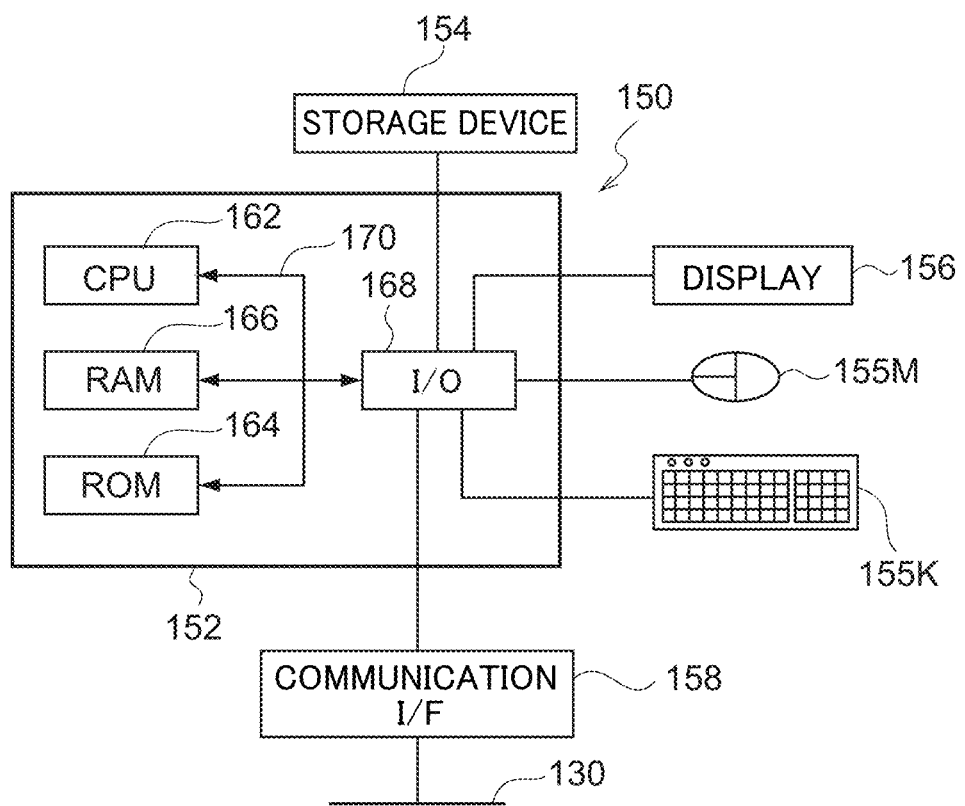
FIG. 4 is a block diagram illustrating a configuration of an electrical system of an image viewer 150.

Explanation follows regarding a configuration of an electrical system of the management server 140, with reference to FIG. 3. As illustrated in FIG. 4, the management server 140 is provided with a computer body 252. The computer body 252 includes a CPU 262, RAM 266, ROM 264, and an input/output (I/O) port 268. A storage device 254, a display 256, a mouse 255M, a keyboard 255K, and a communication interface (I/F) 258 are coupled to the input/output (I/O) port 268. The storage device 254 is, for example, configured by non-volatile memory. The input/output (I/O) port 268 is coupled to the network 130 through the communication interface (I/F) 258. The management server 140 is thus capable of communicating with the ophthalmic device 110, the eye axial length measurement device 120, and the image viewer 150.

The management server 140 stores each data received from the ophthalmic device 110 and the eye axial length measurement device 120 in the storage device 254.

Explanation follows regarding a configuration of an electrical system of the image viewer 150, with reference to FIG. 4. As illustrated in FIG. 4, the image viewer 150 is provided with a computer body 152. The computer body 152 includes a CPU 162, RAM 166, ROM 164, and an input/output (I/O) port 168. A storage device 154, a display 156, a mouse 155M, a keyboard 155K, and a communication interface (I/F) 158 are coupled to the input/output (I/O) port 168. The storage device 154 is, for example, configured by non-volatile memory. The input/output (I/O) port 168 is coupled to the network 130 through the communication interface (I/F) 158. The image viewer 150 is thus capable of communicating with the ophthalmic device 110 and the management server 140.

Figure 5:
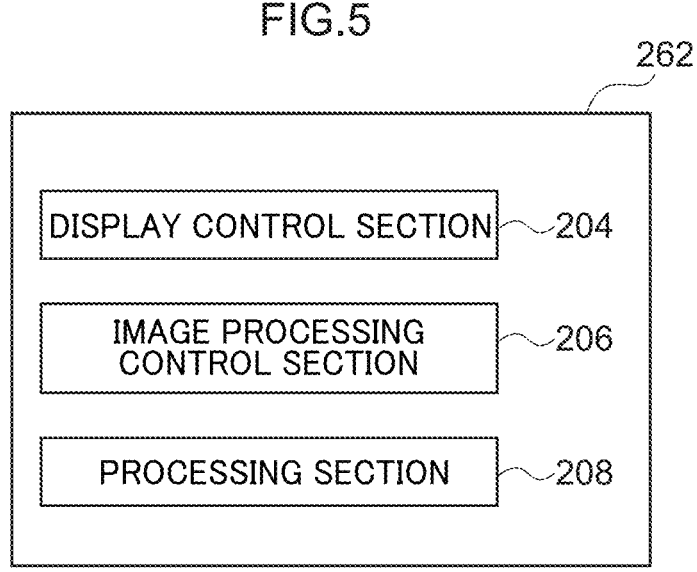
FIG. 5 is a block diagram illustrating functionality of a CPU 262 of a management server 140.

Explanation follows regarding various functions implemented by the CPU 262 of the management server 140 executing the image processing program. As illustrated in FIG. 5, the image processing program includes a display control function, an image processing control function, and a processing function. The CPU 262 functions as the display control section 204, the image processing control section 206, and a processing section 208 illustrated in FIG. 6 by the CPU 262 executing the image processing program that includes these functions.

The image processing control section 206 is an example of a "choroid information acquisition section" and "determination" of the technology disclosed herein. As will be described in detail later, choroid information includes information relating to a choroidal blood vessel (a feature amount of a choroidal blood vessel), and information relating to the choroid structure (a feature amount of a choroidal structure).

Figure 6:
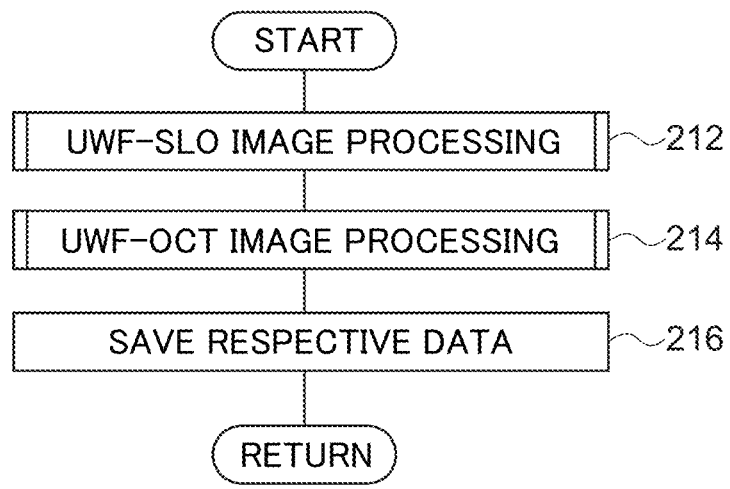
FIG. 6 is a flowchart of an image processing program.

Detailed explanation follows regarding the image processing performed by the management server 140, with reference to FIG. 6. The image processing (image processing method) illustrated in the flowchart of FIG. 6 is realized by the CPU 262 of the management server 140 executing the image processing program.

The image processing control section 206 executes UWF-SLO image processing at step 212, and executes UWF-OCT image processing at step 214. Details regarding the processing of step 212 and step 214 will be described later. At step 216, the processing section 208 saves various data obtained by the processing of step 212 and step 214 in the storage device 254.

Figure 7:
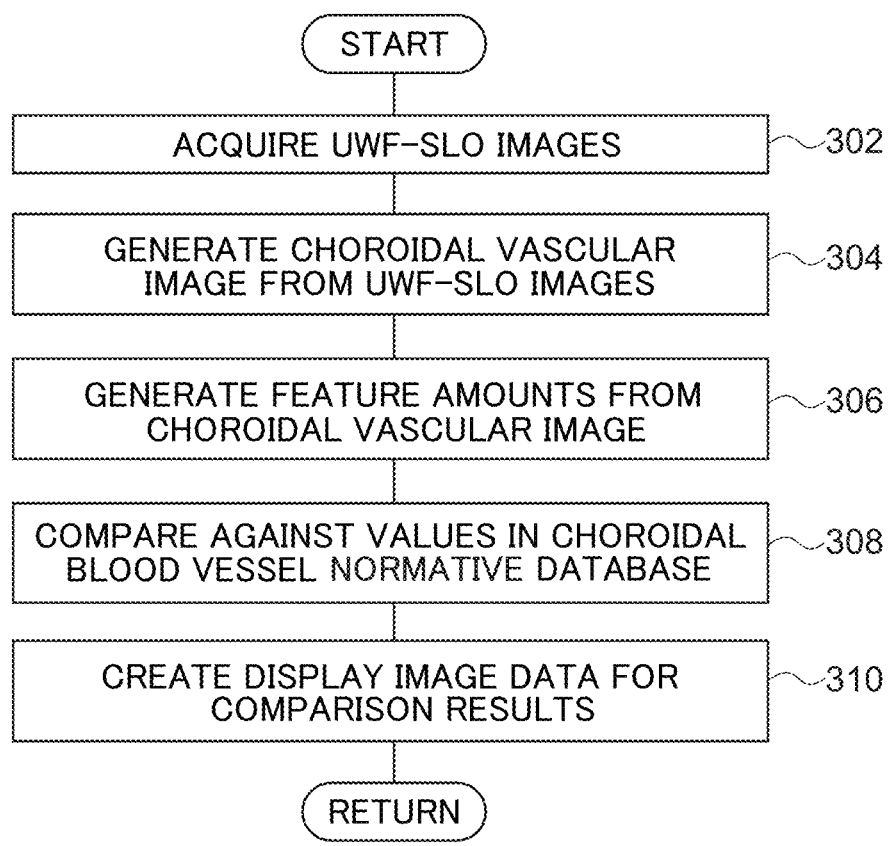
FIG. 7 is a flowchart of UWF-SLO image processing performed at step 212 in FIG. 6.
Figure 8:
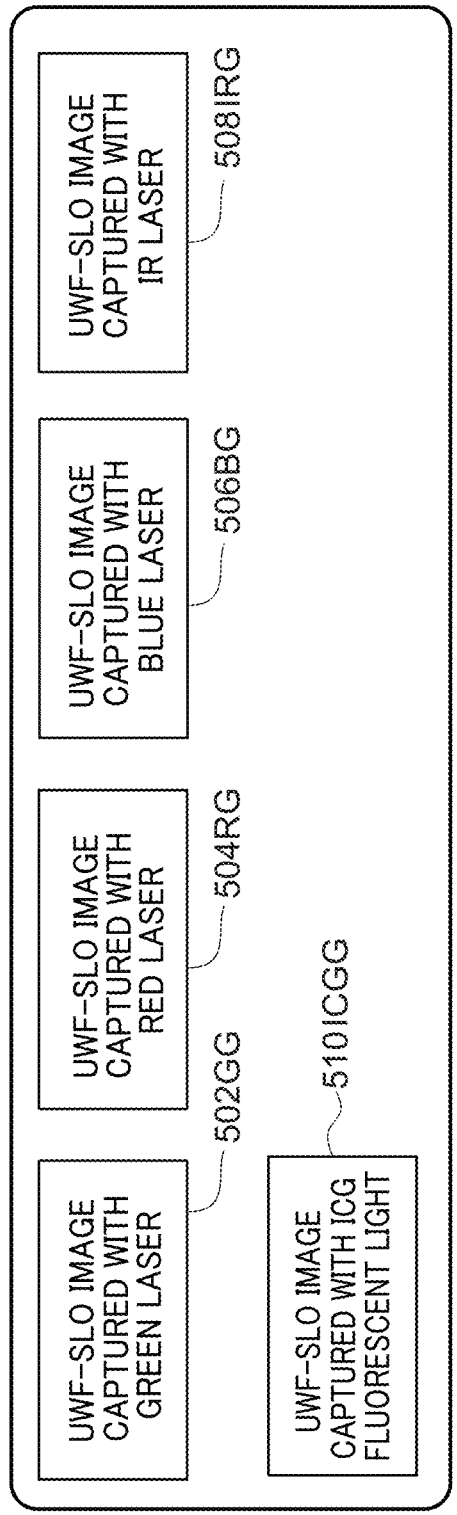
FIG. 8 is a diagram illustrating various types of UWF-SLO images obtained by an ophthalmic device 110.

FIG. 7 is a flowchart illustrating the UWF-SLO image processing of step 212 in FIG. 6. More specifically, the flowchart includes processing to generate choroid information by performing image processing on the UWF-SLO images, to compare the generated choroid information against a normative database, and to generate a display screen to display comparison results. A user is able to determine whether or not the choroid is abnormal based on these comparison results.

First, at step 302 the image processing control section 206 acquires UWF-SLO images from the storage device 254. The UWF-SLO images captured by the ophthalmic device 110 are stored in the storage device 254.

Figure 9:
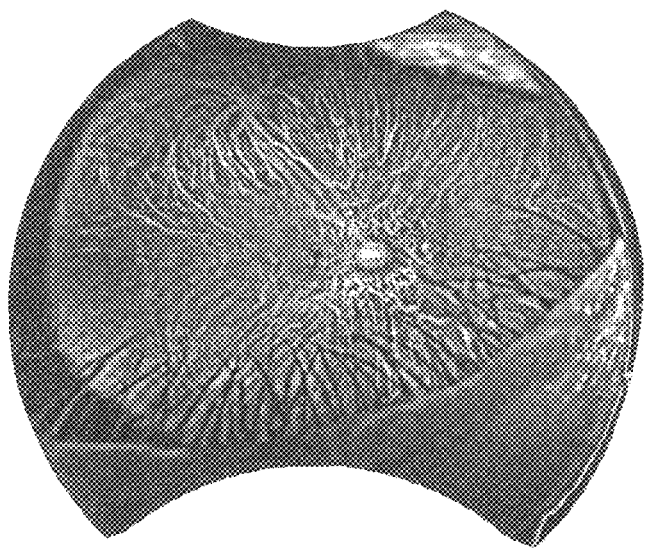
FIG. 9 is a diagram illustrating a choroidal vascular image.

At step 304, the image processing control section 206 creates a choroidal vascular image (FIG. 9) from the acquired UWF-SLO images in the following manner. The choroidal vascular image is an image obtained by performing image processing on the UWF-SLO images to make the choroidal blood vessels visible. The UWF-SLO images subjected to image processing are, for example, a red fundus image and a green fundus image.

First, explanation follows regarding information included in the red fundus image and the green fundus image that is required to generate the choroidal vascular image.

The structure of an eye is one in which a vitreous body is covered by plural layers of differing structure. The plural layers include, from the vitreous body at the extreme inside to the outside, the retina, the choroid, and the sclera. Since red light is of longer wavelength, red light passes through the retina and reaches the choroid. The red fundus image 504RG therefore includes information relating to blood vessels present within the retina (retinal blood vessels) and information relating to blood vessels present within the choroid (choroidal blood vessels). In contrast thereto, due to green light being of shorter wavelength than red light, green light only reaches as far as the retina. The green fundus image 502GG accordingly only includes information relating to the blood vessels present within the retina (retinal blood vessels). This thereby enables a choroidal vascular image (FIG. 9) to be obtained by extracting the retinal blood vessels from the green fundus image 502GG and removing the retinal blood vessels from the red fundus image 504RG. The choroidal vascular image is specifically generated in the following manner.

The image processing control section 206 extracts the retinal blood vessels from the green fundus image 502GG by applying black hat filter processing to the green fundus image 502GG. Next, the image processing control section 206 removes the retinal blood vessels from the red fundus image 504RG by performing an in-painting processing thereon. Namely, position information for the retinal blood vessels extracted from the green fundus image 502GG is employed when performing processing to infill the positions of the retinal blood vessel structure in the red fundus image 504RG using pixel values the same as those of surrounding pixels. The image processing control section 206 then emphasizes the choroidal blood vessels in the red fundus image 504RG by performing contrast limited adaptive histogram equalization processing on the image data of the red fundus image 504RG from which the retinal blood vessels have been removed. The choroidal vascular image illustrated in FIG. 9 was created in this manner. The created choroidal vascular image is stored in the storage device 254.

Figure 10:
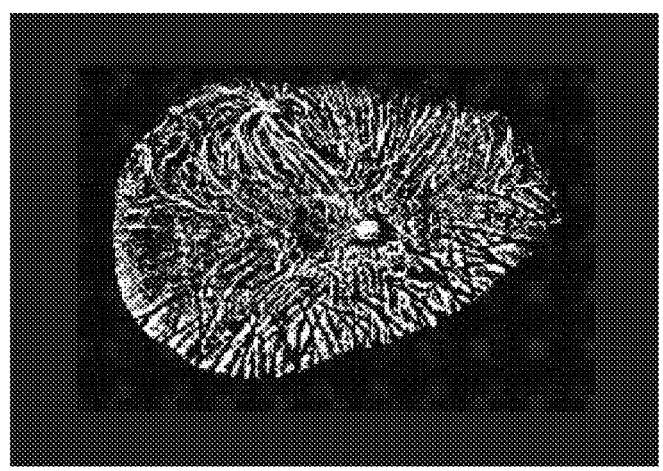
FIG. 10 is a diagram illustrating a choroidal vascular binary image.

Since an eyelid or the like may be included in an image of the choroidal blood vessels, the image processing control section 206 performs processing at step 304 to crop the choroidal vascular image to a fundus region (removing eyelids etc.) so as to generate a choroidal vascular image (see FIG. 10). The choroidal vascular image (FIG. 9) and the choroidal vascular image (FIG. 10) are thus images in which the choroidal blood vessels have been rendered visible that were obtained by performing image processing on the fundus images.

In the above example, the choroidal vascular image is generated from the red fundus image 504RG and the green fundus image 502GG. However, the image processing control section 206 may generate a choroidal vascular image from the green fundus image 502GG and the UWF-SLO image 508IRG. The image processing control section 206 may also generate a choroidal vascular image from the blue fundus image 506BG and one image from out of the red fundus image 504RG or the UWF-SLO image 508IRG.

Furthermore, a choroidal vascular image may also be generated from the UWF-SLO image (video) 510. As described above, the UWF-SLO image (video) 510 is a video image from the time indocyanine green (ICG) that has been injected into a blood vessel reaches the retina until after the indocyanine green (ICG) has passed through the choroid. The choroidal vascular image may be generated from a video image of a period after the indocyanine green (ICG) has passed through the retina and during which the indocyanine green (ICG) is passing through the choroid.

The diameter of blood vessels in the choroid is generally larger than the diameter of blood vessels in the retina. Specifically, blood vessels of a diameter larger than a specific threshold value are choroidal blood vessels. The choroidal vascular image may accordingly be generated by extracting blood vessels from images in the UWF-SLO image (video) 510 taken when the indocyanine green (ICG) is passing through the blood vessels of the retina and the choroid, and then removing any blood vessels with a diameter smaller than the specific threshold value.

Plural choroidal blood vessels are included in the choroidal vascular image. At step 304, the image processing control section 206 further extracts the respective choroidal blood vessels from the created choroidal vascular image.

At step 306, the image processing control section 206 performs image processing on the choroidal vascular image (FIG. 10) to generate feature amounts for the choroidal blood vessel, this being choroid information.

Note that as described later, the choroidal blood vessel feature amounts include (1) a degree of asymmetry in blood vessel flow direction, (2) vortex vein positions and a degree of symmetry in vortex vein positions, (3) histograms and average values of blood vessel diameters at vortex vein vicinity positions, (4) the blood vessel diameters of blood vessels in the choroidal vascular image and a histogram of the blood vessel diameters, and (5) the degree of meandering of each of the choroidal blood vessels.

Detailed explanation follows regarding the choroidal blood vessel feature amounts generated by the image processing performed on the choroidal vascular image.

(1) Processing to Generate the Degree of Asymmetry in Blood Vessel Flow Direction First, explanation follows regarding the degree of asymmetry in the blood vessel flow direction. The degree of asymmetry in the blood vessel flow direction is a degree of asymmetry between choroidal blood vessels corresponding to a first region and a second region obtained by dividing the choroidal vascular image about a specific straight line. Specifically, the degree of asymmetry in the blood vessel flow direction is found in the following manner.

The image processing control section 206 detects the macula M (see also FIG. 12) in the green fundus image 502GG. Specifically, since the macula is a dark region in the green fundus image 502GG, the image processing control section 206 detects as the macula M a region of a specific number of pixels having the smallest pixel values in the above green fundus image 502GG that has been read. A central position of the region that includes the darkest pixels is computed as the coordinates of the position of the macula M, and this is stored in the storage device 254. The image processing control section 206 also detects the position of the optic nerve head ONH (see also FIG. 12) in the green fundus image 502GG. Specifically, the image processing control section 206 detects the position of the optic nerve head in the green fundus image 502GG by performing pattern matching in the green fundus image 502GG for predetermined images of optic nerve head, computes the detected position as the coordinates of the position of the optic nerve head ONH, and stores this position in the storage device 254.

The image processing control section 206 reads the macula M coordinates and the optic nerve head ONH coordinates. The image processing control section 206 sets the respective read coordinates on the choroidal vascular image, and establishes a straight line LIN (see FIG. 11) on the choroidal vascular image to connect the macula M and the optic nerve head ONH together. Note that since the choroidal vascular image is generated from the green fundus image and the red fundus image, the coordinates of the macula M and the coordinates of the optic nerve head ONH as detected in the green fundus image match those of the position of the macula M and the position of the optic nerve head ONH in the choroidal vascular image.

The image processing control section 206 then rotates the choroidal vascular image to make the straight line LIN horizontal.

Figure 11:
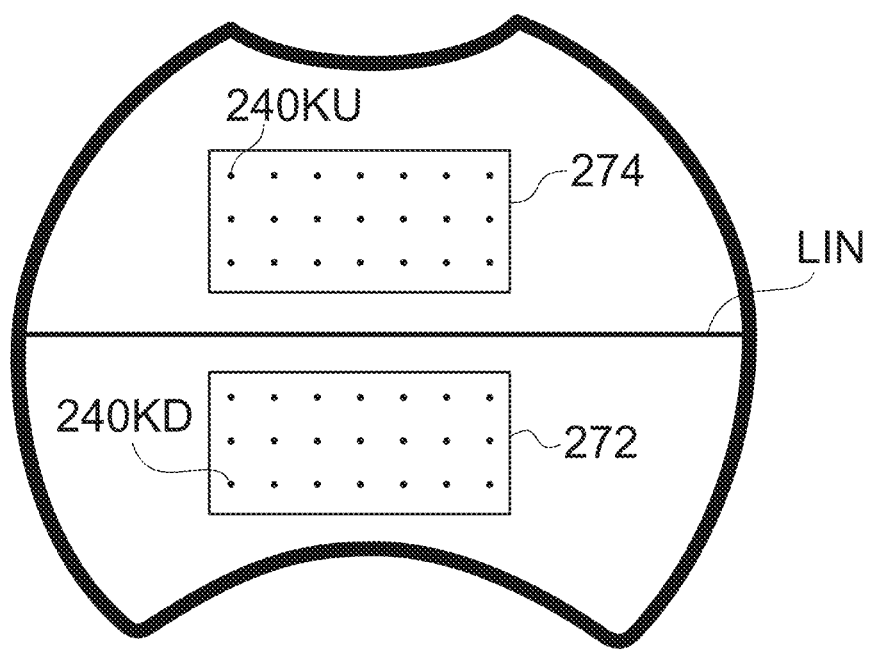
FIG. 11 is a diagram illustrating a first region 274 and a second region 272 set by a straight line LIN established on a choroidal vascular image, with analysis points set in each region.

Analysis points are then set in the following manner. As illustrated in FIG. 11, a first region 274 and a second region 272 of the choroidal vascular image are established by the straight line LIN. Specifically, the first region is positions above the straight line LIN, and the second region is positions below the straight line LIN.

The image processing control section 206 then places analysis points 240KU at positions in a grid pattern at uniform intervals from each other in the first region 274, with M (a natural number) rows in the up-down direction and N (a natural number) columns in the left-right (horizontal) direction. In FIG. 11, the number of analysis points in the first region 274 is M(3)×N(7)(=L: 21).

The image processing control section 206 then places analysis points 240KD in the second region 272, at positions with line symmetry about the straight line LIN to the analysis points 240KU placed in the first region 274.

The image processing control section 206 computes the blood vessel flow direction of the choroidal blood vessels at each of the analysis points. Specifically, the image processing control section 206 repeats the following processing for each of the analysis points. Namely, as illustrated in FIG. 12, for a central pixel corresponding to an analysis point 242, the image processing control section 206 sets a region (cell) 244 configured by plural pixels centered on this central pixel and around the center image.

The region 244 in FIG. 12 is illustrated after top-to-bottom inversion. This is done to facilitate comparison with a region (cell) 248 that includes an analysis point 246 at the upper side of the region 244 and that forms a pair with the region 244.

The image processing control section 206 then calculates a brightness gradient direction (expressed as an angle from 0° up to but not including 180°, with 0° defined as the direction of the straight line LIN (horizontal line)) for each pixel in the cell 244, based on brightness values of the peripheral pixels to the pixel being calculated. The gradient direction calculation is performed for all of the pixels in the cell 244.

Next, the image processing control section 206 counts the number of pixels inside the cell 244 that have a gradient direction in each of nine bins (with each bin width of 20°), these being bins on 0°, 20°, 40°, 60°, 80°, 100°, 120°, 140°, and 160° with respect to an angle reference line, in order to create a histogram 242H of the counts corresponding to each of the bins. The angle reference line is the straight line LIN. The width of a single bin in the histogram corresponds to 20°. The 0° bin is set with the number (count value) of pixels in the cell 244 having a gradient direction of from 0° up to but not including 10°, or a gradient direction of from 170° up to but not including 180°. The 20° bin is set with the number (count value) of pixels in the cell 244 having a gradient direction of from 10° up to but not including 30°. The count values for the bins 40°, 60°, 80°, 100°, 120°, 140°, and 160° are set in a similar manner. Due to there being nine bins in the histogram 242H, the blood vessel flow direction of the analysis point 242 is defined as being in one of nine types of direction. Note that the resolution of the blood vessel flow direction can be raised by narrowing the width of each bin and increasing the number of bins.

The count values of the respective bins (the vertical axis of the histogram 242H) are normalized when creating the histogram 242H for the analysis point 242.

Next, the image processing control section 206 identifies the blood vessel flow direction of the analysis point from the histogram 242H. Specifically, the angle with the smallest count value is identified as the blood vessel flow direction of the analysis point 242. Note that the reason the gradient direction with the smallest count is taken as the blood vessel flow direction is the following. Namely, the brightness gradient is small along the blood vessel flow direction, and the brightness gradient is large in other directions (for example, there is a large difference between a brightness of a blood vessel and a brightness of something other than a blood vessel). Accordingly, there will be a small count value for the bin corresponding to the blood vessel flow direction in a brightness gradient histogram created for all the respective pixels.

A cell 248 is similarly set for the analysis point 246 and a histogram 246H is created therefor. The 160° bin is identified as being the bin having the smallest count value out of the bins for the histogram 246H. The blood vessel flow direction of the analysis point 246 is thus identified as being 160°.

Figure 13:
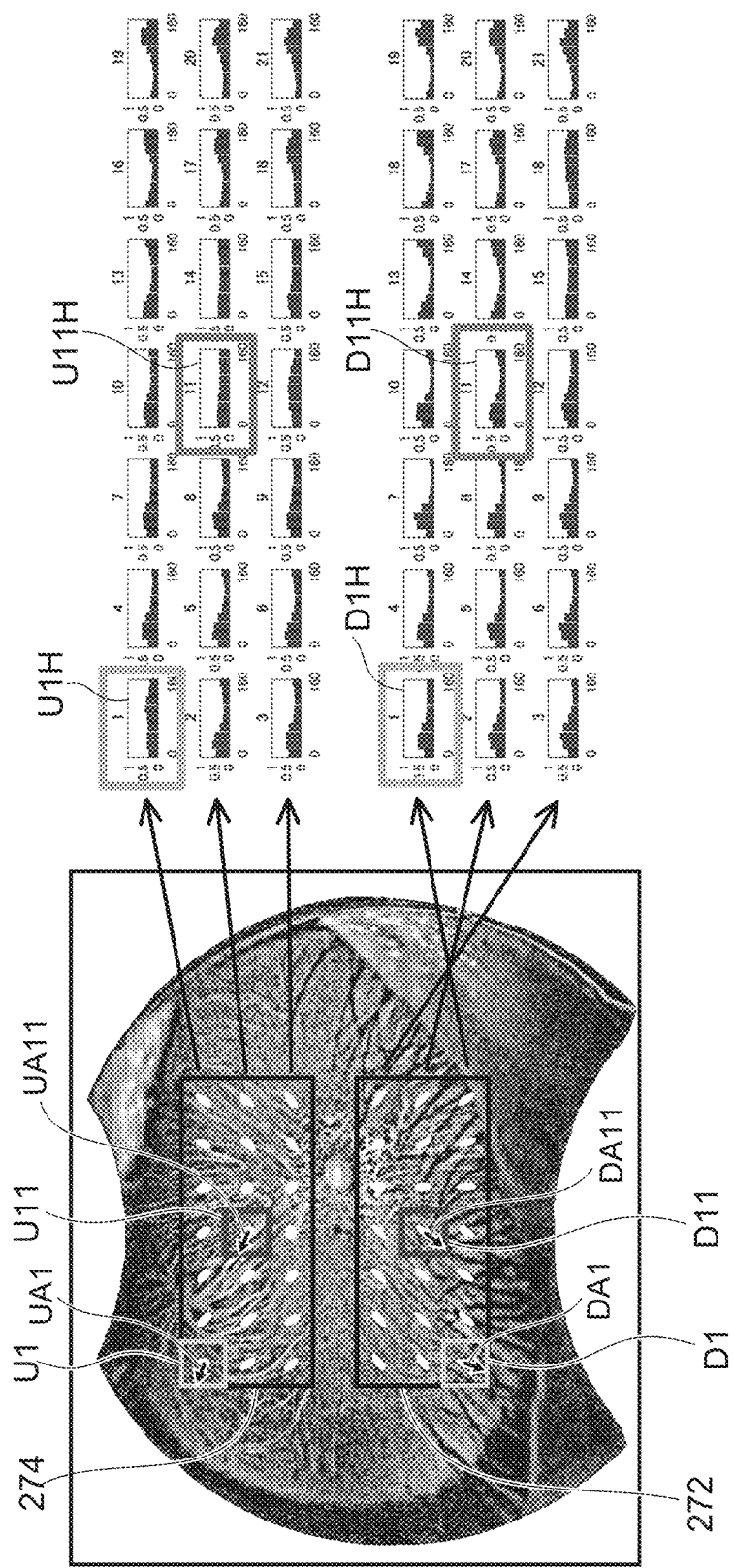
FIG. 13 is a diagram illustrating histograms for respective analysis points.

The above processing is performed for all of the analysis points in the first region and the second region so as to identify the blood vessel flow direction of each of the analysis points set in the choroidal vascular image. Namely, histograms are derived for each of the analysis point, as illustrated in FIG. 13.

The image processing control section 206 reads the respective upper and lower analysis points (in the first region and the second region), and the blood vessel flow directions of these points. Specifically, the image processing control section 206 reads the respective analysis points and the blood vessel flow direction of these points for each analysis point pair having line symmetry about the straight line LIN.

The image processing control section 206 computes a value expressing the asymmetry for each pair of analysis points having line symmetry about the straight line LIN. The value used to express asymmetry is the difference between the respective blood vessel flow directions therein, with this difference being found using the histograms for each analysis point in each of the pairs. A difference Δh is found between the counts for each bin in the respective pair of histograms, and Δh is squared. ΣΔh², i.e. the sum of the Δh² over all bins is then calculated. Larger values of ΣΔh² mean that the difference between the shapes of the histograms is greater, and there is accordingly more asymmetry. Smaller values of ΣΔh² mean the histograms more closely resemble each other, and so the asymmetry is accordingly less.

Note that the value employed to express asymmetry is not limited to the sum of the squared errors in the histograms at the respective pairs of analysis points. For example, representative angles may be decided from the histograms at the respective pairs of analysis points and an absolute difference between the representative angles computed therefrom.

The image processing control section 206 finds an overall average value of the values expressing the asymmetry at the respective pairs as a blood vessel flow direction degree of asymmetry. The thus found blood vessel flow direction degree of asymmetry is stored in the RAM 266.

(2) Processing to Generate Vortex Vein Positions and Vortex Vein Position Symmetry Explanation follows regarding processing to generate vortex vein positions. Vortex veins are drains for blood that flowed into the choroid, with four to six thereof being present on the equator of the eyeball posterior toward the posterior pole of the eyeball.

Figure 14:
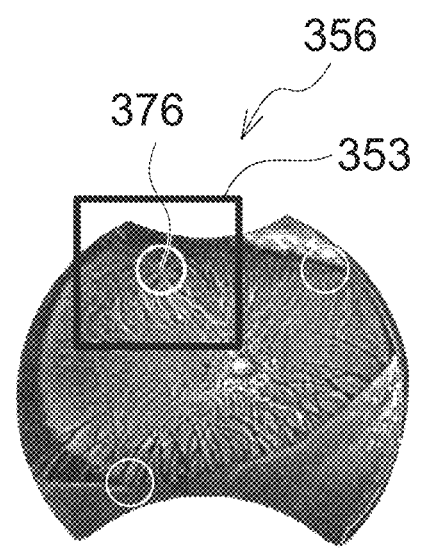
FIG. 14 is a diagram illustrating a choroidal vascular image 356 in which the positions of vortex veins are overlaid on the choroidal vascular image.

FIG. 14 illustrates a choroidal vascular image 356 in which the positions of vortex veins have been overlaid on the choroidal vascular image. A vortex vein position 376 is encircled in the choroidal vascular image 356. Three vortex veins are encircled in FIG. 14.

The choroidal blood vessels are extracted from the choroidal vascular image, and the vortex vein positions are computed based on the directions of flow of the each choroidal blood vessel. Due to the vortex veins being drains for blood flow, there are plural blood vessel connected to each of the vortex veins. Namely, the vortex vein positions can be found by searching the choroidal vascular image for points where the flow directions of plural blood vessels converge.

The image processing control section 206 identifies the number of vortex veins, and identifies the coordinates of each of the vortex veins in the choroidal vascular image as respective vortex vein positions. The image processing control section 206 then stores the number of vortex veins and the respective vortex vein positions in the RAM 266.

The image processing control section 206 further computes a degree of symmetry of the vortex vein positions.

Generally vortex veins are present at positions with line symmetry about the straight line LIN described above. The degree of symmetry of the vortex vein positions may be defined as the amount of displacement of a vortex vein position at the lower side of the straight line LIN with respect to a vortex vein position at the upper side of the straight line LIN (or conversely, the vortex vein position at the lower side of the straight line LIN may be employed as the reference). Namely, a point having line symmetry about the straight line LIN to the vortex vein position at the upper side is found, and then an amount of displacement is found between this point of line symmetry and the actual vortex vein position at the lower side. The image processing control section 206 stores this displacement amount as the degree of symmetry of the vortex vein positions in the RAM 266.

(3) Histogram of Blood Vessel Diameters at Vortex Vein Vicinity Positions and Average Value Thereof Explanation follows regarding a histogram of blood vessel diameters at vortex vein vicinity positions and average value thereof.

The image processing control section 206 binarizes the choroidal vascular image (FIG. 10) by binarizing the pixel value of each pixel based on a specific threshold value, thereby creating a non-illustrated choroidal vascular binary image. The choroidal vascular binary image is an image in which the choroidal blood vessels are rendered visible (pixels in regions corresponding to choroidal blood vessels are white, and pixels in regions other than choroidal blood vessels are black). The image processing control section 206 extracts images of specific regions (vicinities) in the choroidal vascular binary image that include a vortex vein position. The choroidal vascular binary image is created by the image processing control section 206 binarizing each of the pixel values for the pixels in the choroidal vascular image based on the specific threshold value. This choroidal vascular binary image is an image in which a choroidal blood vessel is visualized (pixels in a region corresponding to the choroidal blood vessel are white and pixels in a region other than the choroidal blood vessel are black).

Figure 15:
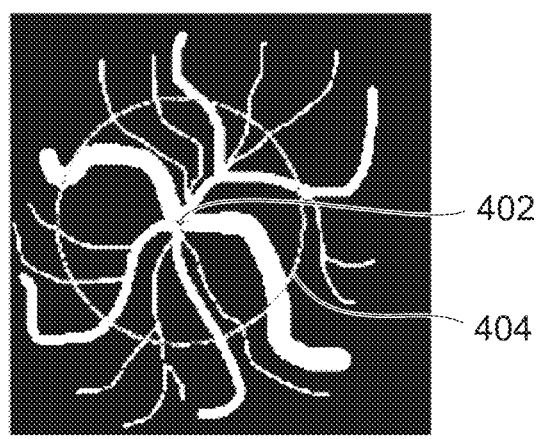
FIG. 15 is a diagram illustrating setting of a circle 404 of a specific radius centered on a vortex vein position 402 in a choroidal vascular binary image.

As illustrated in FIG. 15, the image processing control section 206 sets a circle 404 having a specific radius centered on a vortex vein position 402 on the choroidal vascular binary image. The specific radius of the circle 404 is 6 mm. The radius of the circle 404 may be set between 2 mm and 20 mm depending on the analysis required.

Figure 16:
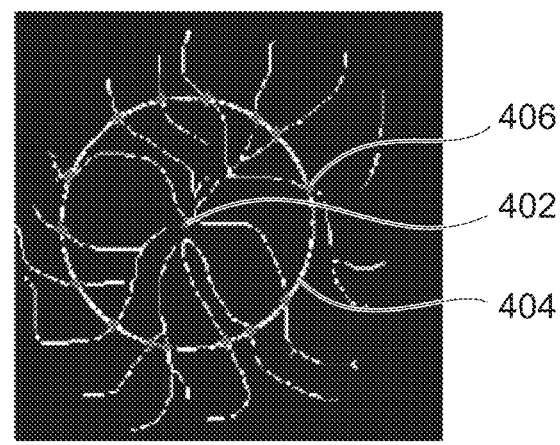
FIG. 16 is a diagram illustrating intersections 406 between the circle 404 and thinned lines.
Figure 17:
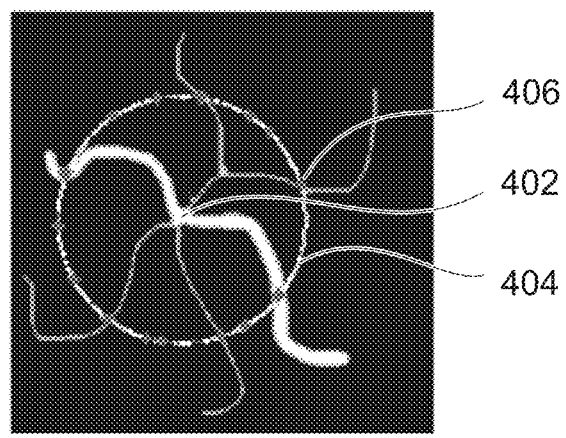
FIG. 17 is a diagram illustrating a distance image.

The image processing control section 206 performs processing to make lines thinner in the image of the specific region of the choroidal vascular binary image that includes the vortex vein position. As illustrated in FIG. 16, the image processing control section 206 detects intersections 406 between the circle 404 and the thinned lines. As illustrated in FIG. 17, the image processing control section 206 generates a distance image from the image of the specific region of the choroidal vascular binary image that includes the VV position. The distance image is an image in which the brightness of lines gradually increases on progression from the edges of the lines toward the center thereof, and, according to the thickness of the lines in the image of the specific region of the choroidal vascular binary image that includes the VV position, the brightness of a central position of the line is brighter the greater the thickness of the line.

The image processing control section 206 extracts from the distance image a brightness value for a position corresponding to each intersection 406. The image processing control section 206 then converts the brightness values of the respective intersections 406 into blood vessel diameters according to a look-up table stored in advance in the storage device 254 and expressing correspondence relationships between pixel brightness and blood vessel diameter.

Figure 18:
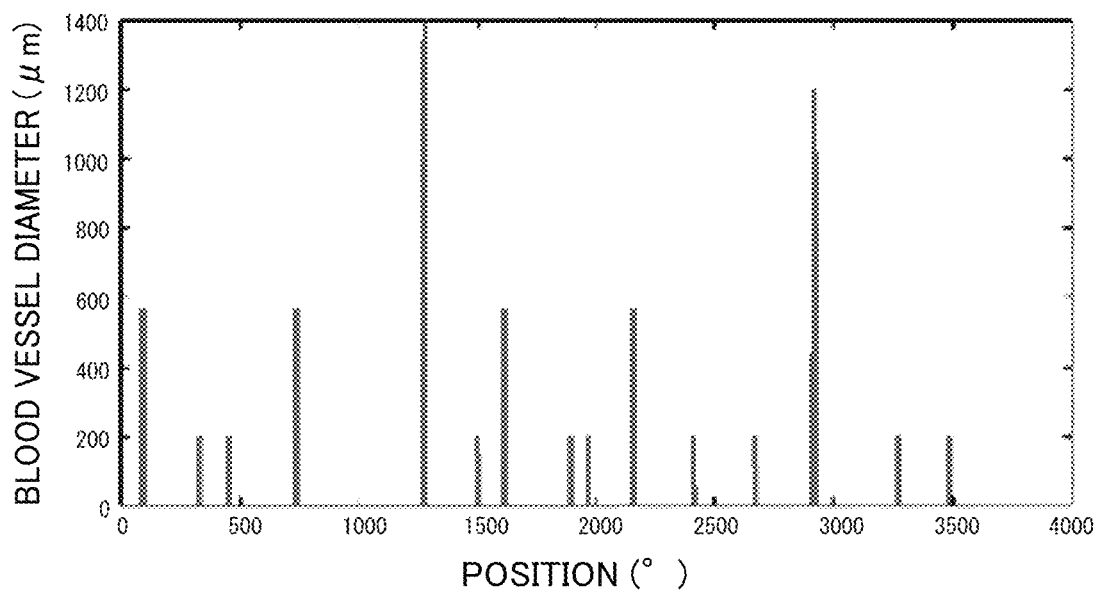
FIG. 18 is a diagram illustrating a graph with an angle of positions of intersections from a specific position on a circle (for example the uppermost edge of the circle) on the horizontal axis, and blood vessel diameters at the intersections on the vertical axis.

As illustrated in FIG. 18, the image processing control section 206 creates a graph with an angle of each position of the intersections 406 from a specific position on the circle (for example the uppermost edge of the circle) on the horizontal axis, and the blood vessel diameter at the respective intersection 406 on the vertical axis. This graph enables the thicknesses of blood vessels and the direction the blood vessel extends from the vortex vein position 402 to be visualized.

Figure 19:
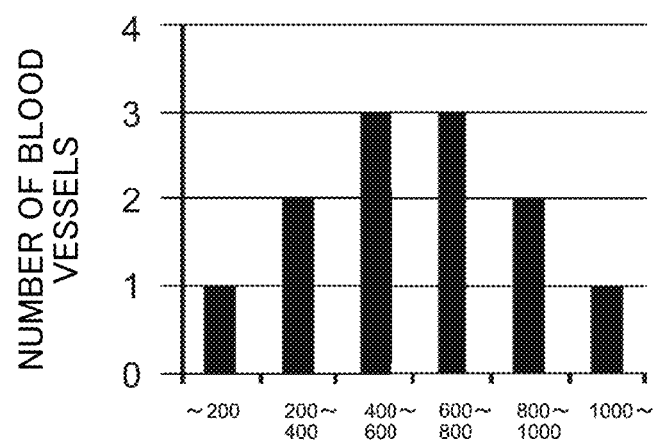
FIG. 19 is a diagram illustrating a histogram of the number of choroidal blood vessels by blood vessel diameter obtained by tallying the blood vessel diameters at the respective intersections to create a histogram with six bins, each bin having a width of 200 µm.

As illustrated in FIG. 19, the image processing control section 206 tallies the blood vessel diameters at the respective intersections 406 and creates a histogram of the number of choroidal blood vessels by blood vessel diameter with six bins each bin having a width of 200 μm. This histogram enables a distribution of thicknesses of blood vessels connected to the vortex vein to be visualized, thereby enabling a rate of blood flow into the vortex veins etc. to be estimated. Moreover, the image processing control section 206 computes an average value of the blood vessel diameters for the specific region (vicinity) including the vortex vein position.

The image processing control section 206 stores the created histogram of the blood vessel diameters at the vortex vein vicinity positions and the average value thereof in the RAM 266.

(4) Computation of Blood Vessel Diameters of Blood Vessels in the Choroidal Vascular Image and Generation of Blood Vessel Diameter Histogram Explanation follows regarding computation of blood vessel diameters of blood vessels in the choroidal vascular image and a histogram of blood vessel diameter. The image processing control section 206 identifies plural choroidal blood vessels in the choroidal vascular binary image described above. The image processing control section 206 then computes the blood vessel diameter for each of the choroidal blood vessels in a similar manner to in the computation processing for the blood vessel diameters in the vicinity of the vortex veins as described above. The image processing control section 206 then calculates the blood vessel diameters of the plural choroidal blood vessels.

The image processing control section 206 then generates a blood vessel diameter histogram from the blood vessel diameters of each of the choroidal blood vessels.

The image processing control section 206 stores the created blood vessel diameter histogram and an average value of the blood vessel diameters of the blood vessels in choroidal vascular image in the RAM 266.

(5) Degree of Meandering of Choroidal Blood Vessels

Explanation follows regarding the degree of meandering of the respective choroidal blood vessels.

The image processing control section 206 make the lines in the choroidal vascular binary image thinner, and finds curves to express the respective choroidal blood vessels. The image processing control section 206 then finds the curvature of the curves and the number of meandering positions corresponding to each of the choroidal blood vessels.

The image processing control section 206 then stores the curvature of the curves and the number of meandering positions in the RAM 266 as a degree of meandering.

As described above, choroidal blood vessel feature amounts are generated from the choroidal vascular image as choroid information. Not only the choroidal blood vessel feature amounts as described above, but also various other feature amounts of the choroidal blood vessels may be computed by employing the choroidal vascular images and the UWF-SLO image.

Next, at step 308, the image processing control section 206 compares the respective choroidal blood vessel feature amounts against a normative database that is stored in a normative database of feature amounts (see FIG. 23). The image processing control section 206 functions as a decision-making section at step 308. Namely, the image processing control section 206 references a feature amount generated at step 306 against a normative database value (DB data) stored in the normative database (see FIG. 23), executes a normal/abnormal determination function, and executes a function to estimate the progression of disease and to estimate the prognosis (a predicted time until sight is lost or a numerical value expressing the risk of sight loss).

As illustrated in FIG. 23, the normative database includes databases 700A, 700B, . . . for respective conditions as determined by ethnicity, sex, and age. The databases 700A, 700B, . . . are each divided into a section 702 for feature amounts obtained from an SLO image, a section 704 for feature amounts obtained from an OCT image, described later, and an indocyanine green angiography (ICGA) video section 706. The section 702 for feature amounts obtained from an SLO image includes, for each feature amount, a storage region 712 stored with standard values for respective conditions as determined by ethnicity, sex, and age, and a storage region 714 stored with determination conditions. For example, the storage region 712 of the database 700A for a Japanese male in his 20s is stored with standard values for a Japanese male in his 20s. The storage region 714 is stored with fixed ranges centered on nominal values as normal values.

At step 308, the image processing control section 206 determines whether or not the respective feature amounts generated at step 306 are normal values for each feature amount according to the determination conditions as stored in the corresponding storage region 714. The determination result is sometimes notified using words to express attributes such as normal or abnormal, and is sometimes a quantitative value such as a risk of sight loss or a predicted time until sight will be lost. Such quantitative values may be computed by employing a multivariate regression method or the like.

For example, the determination conditions for vortex vein position are nominal values (coordinate values) for each vortex vein position, and normal ranges set for ranges of a specific distance centered on these nominal values (coordinate values). The image processing control section 206 determines whether or not each of the vortex vein positions generated at step 306 falls within a normal range in the vortex vein position determination conditions. Abnormal determination is made unless the vortex vein position falls within a normal range.

Determination conditions for the degree of symmetry of the vortex vein positions are normal ranges set for a specific range centered on a nominal value of a distance ratio and for a specific range centered on a nominal value of an angle ratio. The image processing control section 206 determines whether or not the degree of symmetry distance ratio and angle ratio for the vortex vein positions generated at step 306 fall in their respective normal ranges. Abnormal determination is made when at least one out of the distance ratio or the angle ratio does not fall within the normal range.

Determination conditions for the histogram of diameters of blood vessels in the vortex vein position vicinity are a normal range set for a range centered on a nominal value for the number of choroidal blood vessels of each of the blood vessel diameter ranges. Determination conditions for the average value of the blood vessel diameters in the vortex vein position vicinity are a normal range set for a range centered on nominal values. The image processing control section 206 determines whether or not the number of choroidal blood vessels in each of the blood vessel diameter ranges in the histograms generated at step 306 falls in the normal range, and determines whether or not the blood vessel diameter average value generated at step 306 falls in the normal range. The image processing control section 206 makes an abnormal determination in cases in which the number of choroidal blood vessels in any of the blood vessel diameter ranges does not fall within the normal range, and makes an abnormal determination in cases in which the average value of the blood vessel diameters does not fall within the normal range.

Determination conditions for a histogram of blood vessel diameters in the whole choroidal vascular image are a normal range set for a range centered on a nominal value for the number of choroidal blood vessels in each of the blood vessel diameter ranges. Determination conditions for the average value of the blood vessel diameters of the blood vessels in the choroidal vascular image are a normal range set for a range centered on a nominal value. The image processing control section 206 determines whether or not the number of choroidal blood vessels in each of the blood vessel diameter ranges in the histogram generated at step 306 for the whole choroidal vascular image falls in the normal range, and determines whether or not the average value generated at step 306 for the blood vessel diameter of the blood vessels in the choroidal vascular image falls in the normal range. The image processing control section 206 makes an abnormal determination in cases in which the number of choroidal blood vessels in any of the blood vessel diameter ranges does not fall in the normal range, and makes an abnormal determination in cases in which the blood vessel diameter average value does not fall within the normal range.

Determination conditions for the degree of meandering of the respective choroidal blood vessels are a normal range set for a range centered on a nominal value for a ratio of amplitude to length (cycle) for each of the choroidal blood vessels. The image processing control section 206 determines whether or not the curvature and the number of meanders of the choroidal blood vessels generated at step 306 fall within the normal range. The image processing control section 206 makes an abnormal determination in cases in which the curvature and the number of meanders of the choroidal blood vessels do not fall within the normal range.

Determination conditions for the degree of asymmetry in the blood vessel flow direction are a normal range set for a range centered on a nominal value for the average value of all the values expressing asymmetry for each of the analysis point pairs. The image processing control section 206 determines whether or not the blood vessel flow direction degree of asymmetry generated at step 306 falls in the normal range. The image processing control section 206 makes an abnormal determination in cases in which the average value of all the values expressing asymmetry for each of the analysis point pairs does not fall within the normal range.

Note that a configuration may be adopted in which normal/abnormal determination is made on the basis of the interdependency between the feature amounts instead of being decided according to each of the feature amounts individually. Namely, although the normal/abnormal determination conditions may be set individually for each of the feature amounts, determination may also be made based on multidimensional determination conditions set for multidimensional feature amounts.

Moreover, a configuration may be adopted in which normal/abnormal threshold value determination basis can be adjusted according to the eye axial length of the examined eye.

At step 310, the image processing control section 206 creates display data including the comparison results (determination results) determined at step 308. This display data will be described later.

Detailed explanation follows regarding the UWF-OCT image processing performed at step 214 in FIG. 6.

FIG. 20 is a flowchart illustrating the UWF-OCT image processing performed at step 214 in FIG. 6. At step 602, the image processing control section 206 acquires a UWF-OCT image from the storage device 254. Obviously an OCT image that is not UWF may also be employed.

A fundus OCT image (B-SCAN image) 642 and three-dimensional OCT data 644 (3D-OCT volume data) from a C-SCAN are acquired from the ophthalmic device 110 and stored in the storage device 254.

At step 604, the image processing control section 206 performs segmentation of the OCT image 642, identifies each layer thereof, and identifies the choroid 652 (FIG. 22) based on at least one factor out of the number of the layers or a positional relationship to a retinal pigment epithelium (RPE) layer (the layer of greatest pigmentation density). Note that the choroid 654 may be three-dimensionally identified by performing segmentation of the three-dimensional OCT data 644. An OCT angiography (OCT-A) en face image and a choroid thickness map 656 may also be created from the three-dimensional OCT data 644. The OCT-A data may also be employed to analyze the structure of the choroidal blood vessels.

At step 606, the image processing control section 206 generates feature amounts for the choroid structure, this being choroid information resulting from performing image processing on the OCT image (three-dimensional OCT data).

Note that the feature amounts for the choroid structure include (1) choroid thickness, (2) the nature of processes at the interface between the choroid and the RPE layer, and the waviness of a curve expressing this interface, and (3) a lumen/stroma ratio or the like.

(1) Generation of Choroid Thickness Information

The image processing control section 206 identifies the thickness of the choroid 652 identified in the OCT image 642. A choroid layer 65 is extracted by performing segmentation, and the choroid thickness information is computed by performing image processing thereon. The computed choroid thickness information enables the choroid to be rendered visible on the choroid thickness map 656.

The image processing control section 206 stores the choroid thickness information and the choroid thickness map 656 in the RAM 266.

(2) Generation of Nature of Processes and Waviness at Interface Between Choroid and RPE Layer The image processing control section 206 extracts a curve expressing the interface between the choroid and the RPE layer in the segmented OCT image. The frequency components of the extracted curve are found by Fourier-transformation. The integral (or average value) of high frequency band components is computed as the waviness. The integral (or average value) of low frequency band components is computed as the nature of processes. Note that there is no limitation to performing a Fourier transform on the curve, and a wavelet transform may be performed instead.

Alternatively, the second differential of the curvature of the interface may be calculated, and an average value or an integral thereof may be computed as an index of the nature of processes or the waviness. Alternatively, a difference between, or ratio of, a minimum distance (arc length) between both ends of the interface and a distance (arc length) along the interface may be employed as an index. Alternatively, waves or processes may be counted and the number thereof may be used as an index.

Alternatively, the three-dimensional OCT data 644 may be segmented, the interface between the choroid and the RPE layer identified, and the above analysis method may be applied thereto.

Moreover, the nature of processes and the waviness may be computed for the interface between the choroid and the Bruch's membrane instead for the interface between the choroid and the RPE layer.

(3) Lumen/Stroma Ratio

The lumen refers to the space inside choroidal blood vessels, and appears black in an OCT image. The stroma refers to portions other than the choroid lumen, and appears white in an OCT image. The image processing control section 206 performs segmentation of the OCT image and identifies a choroid region. Pixels in a brightness range of the lumen region are then counted, and the area of the lumen region is then computed by adding up the area for a single pixel over the number of pixels counted. Similarly, pixels in a brightness range of the stroma region are counted, and the area of the stroma region is then computed by adding up the area for a single pixel over the number of pixels counted.

The image processing control section 206 finds the lumen/stroma ratio from the area of the lumen region and the area of the stroma region. The computed ratio is then stored in the RAM 266.

As described above, feature amounts for the choroid structure are generated from the OCT image and three-dimensional OCT data as choroid information. In addition to the choroid structure feature amounts described above, various other choroidal blood vessel feature amounts may be computed by employing data other than the OCT image.

At the next step 608, the image processing control section 206 compares the respective feature amounts obtained from the OCT image against the relevant normative database values stored in the normative database of feature amounts (see FIG. 23). At step 608, the image processing control section 206 functions as a decision-making section. Namely, the image processing control section 206 references the feature amounts generated at step 606 against the relevant normative database values (DB data) stored in the normative database (see FIG. 23) and executes a function to perform normal/abnormal determination, and to estimate the progression of disease and the prognosis (a predicted time until sight is lost or a numerical value expressing the risk of sight loss).

As illustrated in FIG. 23, the respective databases 700A, 700B, . . . each include a section 704 for feature amounts obtained from OCT images. The section 704 for feature amounts obtained from OCT images includes, for each feature amount, the storage region 712 stored with standard values for respective conditions as determined by ethnicity, sex, and age, and the storage region 714 stored with the determination conditions. For example, the storage region 712 of the database 700A for a Japanese male in his 20s is stored with standard values for a Japanese male in his 20s. The storage region 714 is stored with fixed ranges centered on nominal values as normal values.

At step 608, the image processing control section 206 determines whether or not the respective feature amounts generated at step 606 are normal values for the respective feature amounts according to the determination conditions stored in the corresponding storage region 714.

For example, determination conditions for the choroid thickness are nominal values for choroid thickness and normal ranges set as specific ranges centered on the nominal values. The image processing control section 206 determines whether or not the choroid thickness generated at step 606 falls in the normal range for the choroid thickness determination conditions. The image processing control section 206 makes an abnormal determination in cases in which the choroid thickness does not fall within the normal range.

The determination conditions for the nature of processes degree of projection at the interface between the choroid and the RPE layer are a nominal value for the nature of processes and a normal range set as a specific range centered on the nominal value. The image processing control section 206 determines whether or not the nature of processes generated at step 606 falls in the normal range for the nature of processes determination conditions. The image processing control section 206 makes an abnormal determination in cases in which the nature of processes does not fall within the normal range.

Determination conditions for the degree of the waviness of the interface between the choroid and the RPE layer are a nominal value for the waviness and a normal range set as a specific range centered on the nominal value. The image processing control section 206 determines whether or not the waviness generated at step 606 falls in the normal range according to the waviness determination conditions. The image processing control section 206 makes an abnormal determination in cases in which the waviness does not fall within the normal range.

Determination conditions for the lumen/stroma ratio are a nominal value for the lumen/stroma ratio and a normal range set as a specific range centered on the nominal value. The image processing control section 206 determines whether or not the lumen/stroma ratio generated at step 606 falls in the normal range according to the lumen/stroma ratio determination conditions. The image processing control section 206 makes an abnormal determination in cases in which the lumen/stroma ratio does not fall within the normal range.

Note that a configuration may be adopted in which normal/abnormal determination is made on the basis of the interdependency between the feature amounts instead of being decided according to each of the feature amounts individually. Namely, although the normal/abnormal determination conditions may be set individually for each of the feature amounts, determination may also be made based on multidimensional determination conditions set for multidimensional feature amounts.

Moreover, a configuration may be adopted in which normal/abnormal threshold value determination standards can be adjusted according to the eye axial length of the examined eye.

At step 610, the image processing control section 206 creates display data including comparison results (determination results) as determined at step 308. This display data will be described later.

Processing returns to step 216 of FIG. 6 when the processing of step 610 has been finished, and the image processing control section 206 stores the created feature amount data and a display screen in the RAM 266 or the storage device 254. The processing of FIG. 6 is then ended.

Explanation follows regarding a display screen displaying the results of comparing the feature amounts for the examined eye image against the normative database.

Based on user instruction, the display control section 204 creates a display screen 800 (see FIG. 24) to display comparison results from the display data saved at step 216 in FIG. 6 (the results of comparison against the normative database) and an image captured by the ophthalmic device 110. The processing section 208 then transmits display screen data for the display screen 800 to the image viewer 150.

Figure 24:
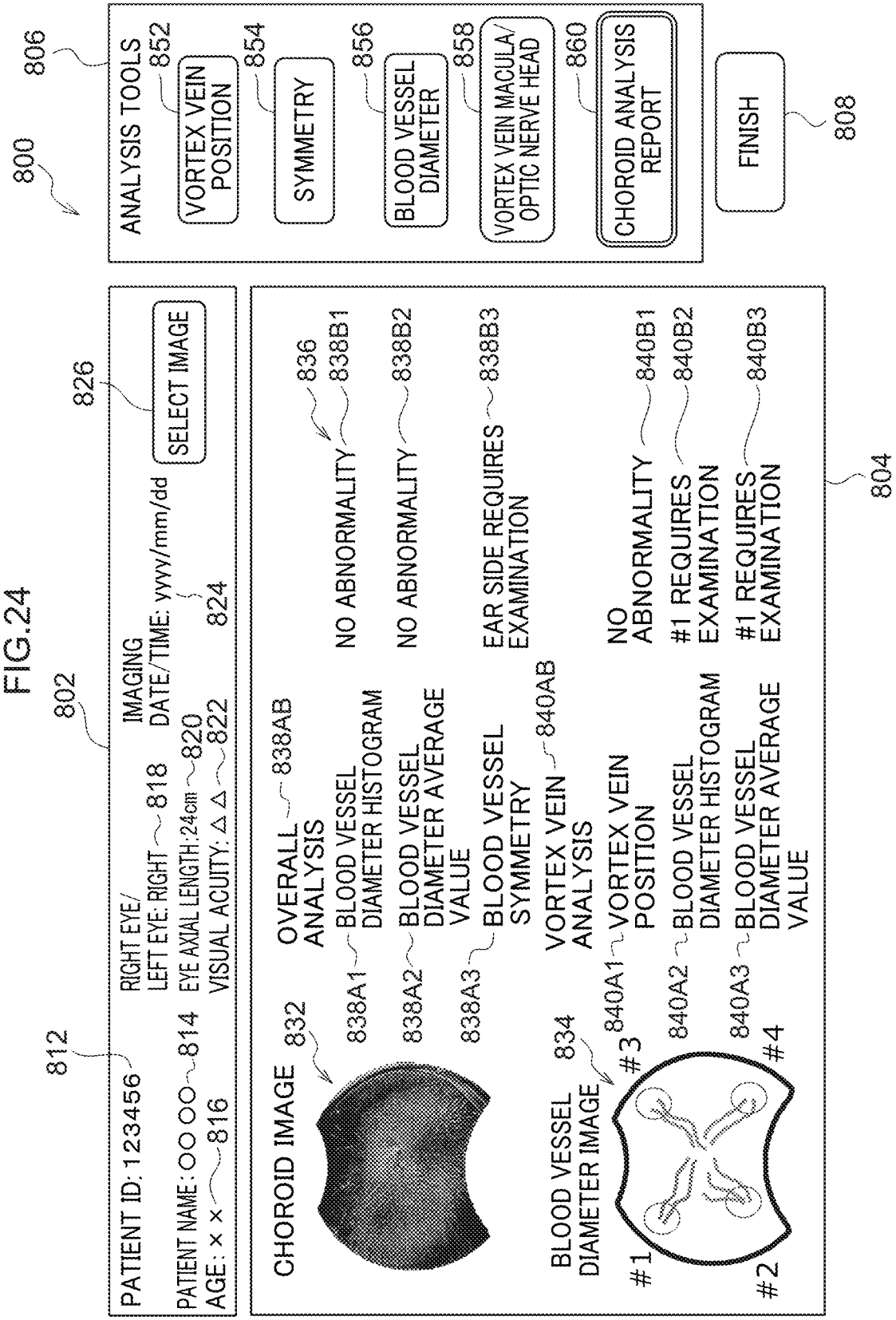
FIG. 24 is a diagram illustrating a display screen 800 for analysis results displayed on a display 156 of an image viewer 150.

On receipt of the display screen data, the image viewer 150 displays the display screen 800 illustrated in FIG. 24 on the display 156 based on the display screen data.

Explanation follows regarding the display screen 800 illustrated in FIG. 24. As illustrated in FIG. 24, the display screen 800 includes a personal information display area 802 to display personal information about a patient, an image display area 804, a choroid analysis tool display area 806, and a finish button 808.

The personal information display area 802 includes a patient ID display field 812, a patient name display field 814, an age display field 816, a right eye/left eye display field 818, an eye axial length display field 820, a visual acuity display field 822, and an imaging date/time display field 824. Each of various types of information is respectively displayed in the display fields 812 to 824. Note that a patient list is displayed on the display 156 of the image viewer 150 when an illustrated patient selection icon is clicked to prompt the user to select the patient for analysis.

The choroid analysis tool display area 806 is an area to display various icons to select plural choroid analysis. A vortex vein position icon 852, a symmetry icon 854, a blood vessel diameter icon 856, a vortex vein-macula/optic nerve head icon 858, and a choroid analysis report icon 860 are provided in the choroid analysis tool display area 806. The vortex vein position icon 852 is used to instruct display of the vortex vein positions. The symmetry icon 854 is used to instruct display of the symmetry analysis points. The blood vessel diameter icon 856 is used to instruct display of analysis results relating to the diameter of choroidal blood vessels. The vortex vein-macula/optic nerve head icon 858 is used to instruct display of analysis results of analyzed positions between the vortex veins, the macula, and the optic nerve head. The choroid analysis report icon 860 is used to instruct display of a choroid analysis report.

The image display area 804 performs first various types of display based on respective comparison results of the feature amounts for the choroidal blood vessels in the choroid information against the normative database values stored in the feature amount normative databases. The image display area 804 performs various types of display based on second each comparison results of the respective feature amounts for the choroid structure in the choroid information against the normative database values stored in the feature amount normative database.

The image display area 804 is a display area to display a choroid analysis report when the choroid analysis report icon 860 is operated. The image display area 804 includes a choroidal vascular image display field 832, a vascular image display field 834, an all-choroidal vascular image analysis result display field 838AB, and a vortex vein analysis result display field 840AB. The all-choroidal vascular image analysis result display field 838AB includes feature amount item display fields 838A1 to 838A3, and analysis result display fields 838B1 to 838B3 corresponding to each item. The vortex vein analysis result display field 840AB includes feature amount item display fields 840A1 to 840A3, and analysis result display fields 840B1 to 840B3 corresponding to each item.

A choroidal vascular image is displayed in the choroidal vascular image display field 832. A vascular image is displayed in the vascular image display field 834. The numbers in the vascular image display field 834 are vortex vein discrimination numbers. The blood vessel diameter of only vortex vein #1 is large. The symmetry is also poor on the ear side (#1 and #2 vortex veins).

Regarding the comparison results of step 308 in FIG. 7, consider a case in which there is no abnormality in the blood vessel diameter histograms nor in the average value blood vessel diameter, but the blood vessel symmetry is abnormal on the ear side. In such a case, "NO ABNORMALITY" would be displayed in the analysis result display field 838B1 corresponding to the blood vessel diameter histogram item display field 838A1. Moreover, "NO ABNORMALITY" would be displayed in the analysis result display field 838B2 corresponding to the blood vessel diameter average value feature amount item display field 838A2. However, "EAR SIDE: REQUIRES EXAMINATION" would be displayed in the analysis result display field 838B3 corresponding to the blood vessel symmetry item display field 838A3.

Regarding the comparison results of step 308 in FIG. 7, consider a case in which there is no abnormality in the vortex vein positions, but the blood vessel diameter histogram for vortex vein #1 is abnormal and the blood vessel diameter average value for vortex vein #1 is abnormal. In such a case, "NO ABNORMALITY" would be displayed in the analysis result display field 840B1 corresponding to the vortex vein position item display field 840A1. However, "#1: REQUIRES EXAMINATION" would be displayed in the analysis result display field 840B2 corresponding to the blood vessel diameter histogram item display field 840A2. Moreover, "#1: REQUIRES EXAMINATION" would also be displayed in the analysis result display field 840B3 corresponding to the blood vessel diameter average value item display field 840A3.

The various types of first display and the various types of second display in the image display area 804 are not limited to the examples illustrated in FIG. 24, and display may be performed based on comparison results for various other feature amounts.

Display may be performed based on the comparison results for whether or not the distance ratio and the angle ratio of the degree of symmetry of the vortex vein positions fall in their respective normal ranges, or display may be performed based on the comparison results for whether or not the curvature and number of meanders of the choroidal blood vessels fall in the normal range.

Display may also be performed based on the comparison results for whether or not the choroid thickness falls in the normal range according to the choroid thickness determination conditions.

Display may also be performed based on the comparison results for whether or not the nature of processes at the interface between the choroid and the RPE layer falls in the normal range according to the nature of processes determination conditions.

Display may also be performed based on the comparison results for whether or not the waviness at the interface between the choroid and the RPE layer falls in the normal range according to the waviness determination conditions.

Display may also be performed based on the comparison results for whether or not the lumen/stroma ratio falls in the normal range according to the lumen/stroma ratio determination conditions.

Display may also be performed based on the results of normal/abnormal determination taking into consideration the interdependency between the feature amounts.

Display based on the respective comparison results may also be performed by using words to express attributes such as normal or abnormal, or display may be performed by using quantitative values such as a risk of sight loss or predicted time until sight is lost.

Explanation follows regarding various modified examples of the technology disclosed herein.

FIRST MODIFIED EXAMPLE

As described above, the normative database (see FIG. 23) includes the databases 700A, 700B, . . . for respective conditions as determined by ethnicity, sex, and age. The databases 700A, 700B, . . . each include an ICGA video section 706. The ICGA video section 706 includes a pulse of pulsatile polyps and a choroidal capillary filling delay as feature amounts. The storage region 712 is stored with standard values, and the storage region 714 is stored with determination conditions.

The normative database may be further stored with analysis results of the standard values for conditions as determined by ethnicity, sex, and age. For example, the mean, variance, kurtosis, skewness, and also higher-order moments of the respective feature amounts, as well as composite feature amount data for the respective feature amounts, and the change over time of the respective feature amounts, may also be stored therein.

Determination conditions are not limited to storing normal ranges, and conditions such as the following may be stored. Stored nominal values may include $3\sigma$, $6\sigma$, or the like computed with reference to the standard deviation $\sigma$ of the population of the normative database, the Fischer's discriminant and Z-factor. A risk percentage conversion equation, a prognosis (time until symptoms appear) conversion equation, or determination attribute data (abnormal/healthy/high risk) may also be stored.

The contents of the normative database may be updated at specific intervals.

SECOND MODIFIED EXAMPLE

Although in the exemplary embodiment and the first modified example described above the feature amounts were analyzed according to determination conditions, the technology disclosed herein is not limited thereto. For example, changes in historical data of previous feature amounts for a given patient may be analyzed according to determination conditions for such changes.

THIRD MODIFIED EXAMPLE

Although in the exemplary embodiments described above the management server 140 executes the image processing program illustrated in FIG. 6, the technology disclosed herein is not limited thereto. A configuration may be adopted in which the image viewer 150 transmits an image processing command to the management server 140, with the management server 140 executing the image processing program of FIG. 6 in response to this command.

FOURTH MODIFIED EXAMPLE

In the exemplary embodiments described above, explanation has been given regarding examples in which a fundus image having an internal illumination angle of approximately 200° is acquired by the ophthalmic device 110. The technology disclosed herein is not limited thereto, and the technology disclosed herein may also be applied in a configuration in which a fundus image having an internal illumination angle of 100° or less is captured by an ophthalmic device, or in a configuration in which a montage image synthesized from plural fundus images is employed.

FIFTH MODIFIED EXAMPLE

Although in the exemplary embodiments described above the fundus image employed is captured by the ophthalmic device 110 provided with an SLO imaging unit, the technology disclosed herein may also be applied to a configuration in which a fundus image captured by a fundus camera capable of imaging choroidal blood vessels, or to an image obtained by OCT angiography, is employed.

SIXTH MODIFIED EXAMPLE

Although in the exemplary embodiments described above asymmetry in the choroidal blood vessel flow direction is analyzed, the technology disclosed herein may be applied in analysis of asymmetry in retinal blood vessel flow direction.

SEVENTH MODIFIED EXAMPLE

Although in the exemplary embodiments described above the management server 140 executes the image processing program, the technology disclosed herein is not limited thereto. For example, the ophthalmic device 110 or the image viewer 150 may execute the image processing program.

EIGHTH MODIFIED EXAMPLE

Although explanation has been given in the exemplary embodiments described above regarding examples in which the ophthalmic system 100 is provided with the ophthalmic device 110, the eye axial length measurement device 120, the management server 140, and the image viewer 150, the technology disclosed herein is not limited thereto. For example, as a first example, a configuration may be adopted in which the eye axial length measurement device 120 is omitted and the ophthalmic device 110 further includes the functionality of the eye axial length measurement device 120. Alternatively, as a second example, a configuration may be adopted in which the ophthalmic device 110 further includes the functionality of at least one out of the management server 140 or the image viewer 150. For example, the management server 140 may be omitted in cases in which the ophthalmic device 110 includes the functionality of the management server 140. In such cases, the image processing program is executed by the ophthalmic device 110 or the image viewer 150. Alternatively, the image viewer 150 may be omitted in cases in which the ophthalmic device 110 includes the functionality of the image viewer 150. As a third example, a configuration may be adopted in which the management server 140 is omitted, and the image viewer 150 executes the functionality of the management server 140.

OTHER MODIFIED EXAMPLES

The data processing as explained in the exemplary embodiments described above are merely examples thereof. Obviously, unnecessary steps may be omitted, new steps may be added, or the processing sequence may be rearranged within a range not departing from the spirit of the present disclosure.

Although explanation has been given in the exemplary embodiments described above regarding an example in which a computer is employed to implement data processing using a software configuration, the technology disclosed herein is not limited thereto. For example, instead of a software configuration employing a computer, the data processing may be executed solely by a hardware configuration such as a field programmable gate array (FPGA) or an application specific integrated circuit (ASIC). Alternatively, a configuration may be adopted in which some processing out of the data processing is executed by a software configuration, and the remaining processing is executed by a hardware configuration.

What is claimed is:

1. An image processing method executed by a processor, the image processing method comprising:
   acquiring choroid information from an image of a fundus of an examined eye; and
   comparing the choroid information against a choroid normative database and determining whether or not there is an abnormality in the fundus,
   wherein the choroid information includes a feature amount relating to choroid structure.

2. The image processing method of claim 1, further comprising outputting a determination result from the determination.

3. The image processing method of claim 1, further comprising outputting a determination result from the determination and outputting the fundus image.

4. The image processing method of claim 1, wherein the fundus image is an SLO image acquired by a scanning laser ophthalmoscope (SLO).

5. The image processing method of claim 1, wherein the fundus image is an OCT image acquired by optical coherence tomography (OCT).

6. The image processing method of claim 1, wherein the choroid information includes a feature amount relating to a choroidal blood vessel.

7. The image processing method of claim 1, wherein the normative database includes at least one standard data out of standard data for a feature amount relating to choroid structure or standard data for a feature amount relating to a choroidal blood vessel.

8. The image processing method of claim 6, wherein:
   the choroid information includes the choroidal blood vessel feature amount; and
   the choroidal blood vessel feature amount includes a feature amount relating to a vortex vein.

9. The image processing method of claim 7, wherein:
   the choroid structure feature amount includes a feature amount relating to choroid thickness.

10. An image processing device comprising memory and a processor coupled to the memory, wherein:
    the processor is configured to
    acquire choroid information from an image of a fundus of an examined eye; and
    compare the choroid information against a choroid normative database and determine whether or not there is an abnormality in the fundus,
    wherein the choroid information includes a feature amount relating to choroid structure.

11. A storage medium being not a transitory signal and stored with an image processing program that causes a computer to execute processing, the processing comprising:
    acquiring choroid information from an image of a fundus of an examined eye; and
    comparing the choroid information against a choroid normative database and determining whether or not there is an abnormality in the fundus,
    wherein the choroid information includes a feature amount relating to choroid structure.

* * * * *